(12) United States Patent
Peng et al.

(10) Patent No.: US 7,834,014 B2
(45) Date of Patent: *Nov. 16, 2010

(54) A$_{2a}$ ADENOSINE RECEPTOR ANTAGONISTS

(75) Inventors: Hairuo Peng, Chestnut Hill, MA (US);
Gang Yao, Sudbury, MA (US); Russell C. Petter, Stow, MA (US);
Gnanasambandam Kumaravel, Westford, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 988 days.

This patent is subject to a terminal disclaimer.

(21) Appl. No.: 10/552,304

(22) PCT Filed: Apr. 9, 2004

(86) PCT No.: PCT/US2004/011009

§ 371 (c)(1),
(2), (4) Date: Jul. 26, 2006

(87) PCT Pub. No.: WO2004/092173

PCT Pub. Date: Oct. 28, 2004

(65) Prior Publication Data

US 2007/0173505 A1    Jul. 26, 2007

Related U.S. Application Data

(60) Provisional application No. 60/461,484, filed on Apr. 9, 2003.

(51) Int. Cl.
*C07D 487/04* (2006.01)
*C07D 403/04* (2006.01)
*C07D 403/06* (2006.01)
*C07D 403/14* (2006.01)
*A61K 31/53* (2006.01)
*A61P 25/16* (2006.01)

(52) U.S. Cl. ............... 514/246; 544/207; 544/209; 544/212

(58) Field of Classification Search ........ 544/207, 544/209, 212; 514/246
See application file for complete search history.

(56) References Cited

U.S. PATENT DOCUMENTS

| | | | |
|---|---|---|---|
| 4,739,053 A | 4/1988 | Albert et al. | |
| 5,204,353 A | 4/1993 | Meier | |
| 5,356,894 A | 10/1994 | Rodney et al. | |
| 5,458,135 A | 10/1995 | Patten et al. | |
| 5,747,496 A | 5/1998 | Cox et al. | |
| 6,005,109 A | 12/1999 | Faraci et al. | |
| 6,107,301 A | 8/2000 | Aldrich et al. | |
| 6,197,788 B1 | 3/2001 | Fletcher et al. | |
| 6,583,156 B1 | 6/2003 | Gillespie et al. | |
| 6,608,085 B1 | 8/2003 | Gillespie et al. | |
| 6,787,541 B1 | 9/2004 | Gillespie et al. | |
| 7,285,550 B2 * | 10/2007 | Vu et al. ............ | 514/245 |

FOREIGN PATENT DOCUMENTS

| | | |
|---|---|---|
| EP | 0390112 | 10/1990 |
| EP | 0459702 | 12/1991 |
| EP | 0496617 | 7/1992 |
| EP | 0515107 | 11/1992 |
| EP | 0666079 | 8/1995 |
| EP | 0667349 | 8/1995 |
| EP | 0976753 | 2/2000 |
| EP | 0976755 | 2/2000 |
| EP | 0992510 | 4/2000 |
| EP | 1221444 | 1/2001 |
| EP | 1116722 | 7/2001 |
| EP | 1300147 | 4/2003 |
| FR | 223066 | 5/1974 |
| JP | 56131586 | 10/1981 |
| JP | 56131587 | 10/1981 |
| JP | 59062595 | 4/1984 |
| JP | 60140335 | 7/1985 |
| JP | 04036284 | 2/1992 |
| WO | WO9320078 | 10/1993 |
| WO | WO9413643 | 6/1994 |
| WO | WO9413677 | 6/1994 |
| WO | WO9417803 | 8/1994 |
| WO | WO9713676 | 4/1997 |
| WO | WO9901439 | 1/1999 |
| WO | WO9901454 | 1/1999 |
| WO | WO9943678 | 2/1999 |
| WO | WO9921617 | 5/1999 |
| WO | WO9940091 | 8/1999 |

(Continued)

OTHER PUBLICATIONS

Baraldi et al., European Journal of Medicinal Chemistry 38: 367-382, 2003.*
Koretskaya et al., Khim.-Farm. Zh. I (1968) 2(6) 5-12.
Mamaev et al., Getertsikl, Soedin, (1971) 7, 535.
Pendergast et al., J. Chem. Soc. Perkin. Trans. (1973) 1, 2759-2763.

(Continued)

*Primary Examiner*—Venkataraman Balasubramanian
(74) *Attorney, Agent, or Firm*—Lando & Anastasi, LLP

(57) ABSTRACT

The invention is based on the discovery that compounds of formula (I) possess unexpectedly high affinity for the A$_{2a}$ adenosine receptor, and can be useful as antagonists thereof for preventing and/or treating numerous diseases, including Parkinson's disease. In one embodiment, the invention features a compound of formula (I).

(I)

27 Claims, No Drawings

FOREIGN PATENT DOCUMENTS

| | | |
|---|---|---|
| WO | WO9948903 | 9/1999 |
| WO | WO9962518 | 12/1999 |
| WO | WO0017201 | 3/2000 |
| WO | WO0061586 | 10/2000 |
| WO | WO0102400 | 1/2001 |
| WO | WO0102409 | 1/2001 |
| WO | WO0162233 | 8/2001 |
| WO | WO03020723 | 3/2003 |
| WO | WO03048163 | 6/2003 |
| WO | WO03068776 | 8/2003 |
| WO | WO2004029056 | 4/2004 |

OTHER PUBLICATIONS

Machon et al., J. Pharmacol. Pharm. (1976) 28, 511.
Higashino et al., Chem Pharm Bull 24, 238-52 (1976).
Higashino et al., Chem Pharm Bull 24, 3120-34 (1976).
Hayashi et al., Yakugaku Zasshi 98, 891 (1978) Abstract.
Robev et al., Dokl. Bolg. Akad. Nauk. (1978) 31; 1131-1134.
Higashino et al., Chem. Pharm. Bull. (1979) 27, 2431.
Higashino et al., Chem. Pharm. Bull. (1979) 27, 3176.
Higashino et al., Fukusokan Kagaku Toronkai Koen Yoshishu, 12th, 1979, 171-5 (Japanese language Conference Report).
Press et al., J. Org. Chem. 48, 4605 (1983).
Schechter et al (1985) J Clin Pharmacol 25, 276.
Higashino et al., Chem Pharm Bull 33, 950 (1985).
Bruns et al., (1986) Mol. Pharmacol. 29: 331-346.
Higashino et al., Chem Pharm Bull 34, 4352 (1986).
Higashino et al., Chem Pharm Bull 34, 4569 (1986).
Molina et al., Tetrahedron Letters (1987) 28, 4451-4454.
Higashino et al., Chem Pharm Bull 35, 4078 (1987).
Jaskolski et al., Acta Crystallogr Sect. C, (1987) C43, 2110-2113.
Molina et al., J. Org. Chem., (1988) 53, 4653-63.
Miyashita et al., Chem Pharm Bull 38, 230(1990).
Hamamichi et al., J. Heterocycl. Chem (1990) 31, 321.
Hamamichi et al., J. Heterocycl. Chem (1990) 27, 835.
Skalski et al., Can. J. Chem (1990) 68, 2164-2170.
Jacobsen et al., J. Med. Chem. (1992) 35(3), 407-423.
Chemical Abstracts, V. 118, No. 3 (1993) Abstract # 22077 Suzuki, Hitomi et al (J. Org. Chem (1993) 58(1) 241-4).
Chemical Abstracts, V. 121, No. 9 (1994) Abstract # 108677 Bouillon et al (Heterocycles (1994) 37(2) 915-32).
Gunderson, Tetrahedron Lett (1994) 35, 3155.
Colotta et al., Eur. J. Jed. Chem. (1995) 30(2), 133-139.
Gundersen et al., Tetrahedron Letters (1995) 36(11), 1945-1948.
Stevenson et al., Tetrahedron Lett. (1996) 37, 8375-8378.
Langli et al., Tetrahedron, vol. 52, Issue 15, Apr. 8, 1996, pp. 5625-5638.
Bertorelli et al (1996) Drug Development Research 37, Issue 2, pp. 65-72.
Prassad et al., Tetrahedron (1997) 53, 7237-7254.
Chebib et al., Bioorganic & Med. Chem Lett (1997) 5(2) 311-322.
Biraldi et al., J. Med. Chem. (1998) 41, 2126-2133.
Francis et al., J. Med. Chem. (1998) 31, 1014-1020.
Monopoli et al. (1998) J Pharmacol Exp Ther 285 (1): 9.
Kim et al., Arch. Pharmacal. Res. (1998) 21, 458-464.
Molina et al., J. Org. Chem. (1998) 53, 4653-4663.
Suzuki et al., Chem Pharm Bull 46, 199 (1998).
Monopoli et al (1998) NeuroReport 9, 3955-3959.
Strappaghetti et al, Eur. J. Med. Chem (1998) 33, 501-508.
Chorvat et al., J. Med. Chem. (1999) 42(5), 833-848.
Betti et al., *Eur. J. Med Chem* (1999) 34(10) 867-875.
Cocuzza et al., Bioorganic & Med. Chem Lett (1999) 9(7) 1063-1066.
Fredholm et al., (1999) Pharmacol Rev. 51, 83-133.
Kopf et al. (1999) Psychopharmacol., 146, 214-219.
Li et al (1999) Experimental Eye Research 68, 9-17.
Svenningsson et al (1999) Progress in Neurobiology 59, 355-396.
Alarcon et al, Tetrahedron Lett (2000) 41, 7211-7215.
Alarcon et al, Bioorg Med Chem Lett (2001) 11, 1855-1858.
Stone et al., (2001) Drug Development Research 52, 323.
Scammell et al., (2001) Neuroscience 107, 653.
El Yacoubi et al., (2001) British Journal of Pharmacology 134, 68-77.
Kase (2001) Bioscience, Biotechnology, and Biochemistry 65, 1447-1457.
Behan et al., (2002) British Journal of Pharmacology (2002) 135, 1435-1442.
Ikeda et al (2002) J Neurochem. 80, 262-70.
Bastia et al., (2002) Neuroscience Letters 328, 241-244.
Hauser et al (2003) Neurology 61 297.
Urade et al (2003) Neurology 2003;61:S94-S96.
Varani et al. (2003) FASEB J. 17, 2148-2150.
Dall'lgna et al., (2003) Br J Pharmacol 138: 1207-1209.
Chase et al., (2003) Neurology 2003;61:S107-S111.
Bara-Jimenez et al., Neurology 2003 61: 293-296.
Bailey et al. J. Neurosci. 22 (21): 9210-9220.

* cited by examiner

$A_{2a}$ ADENOSINE RECEPTOR ANTAGONISTS

This application is 371 of PCT/US04/11009, filed Apr. 9, 2004, which claims benefit of U.S. Provisional Application No. 60/461,484, filed on Apr. 9, 2003.

BACKGROUND OF THE INVENTION

Adenosine is a ubiquitous biochemical messenger. Adenosine binds to and activates certain seven transmembrane-spanning G-protein coupled receptors, eliciting a variety of physiological responses. Adenosine receptors are divided into four known subtypes (i.e. $A_1$, $A_{2a}$, $A_{2b}$, and $A_3$). These receptor subtypes mediate different and sometimes opposing effects. In general, activation of the adenosine $A_{2a}$ or $A_{2b}$ receptor leads to an increase in cellular cAMP levels, while activation of the adenosine $A_1$ or $A_3$ receptor leads to a decrease in cellular cAMP levels. $A_{2a}$ adenosine receptors are abundant in the basal ganglia, a region of the brain associated with the pathphysiology of Parkinson's disease. For reviews concerning $A_{2a}$ adenosine receptors, see, e.g., Moreau et al., Brain Research Reviews 31:65-82 (1999) and Svenningsson et al., Progress in Neurobiology 59:355-396 (1999). For a discussion of the role and regulation of adenosine in the central nervous system, see, e.g., Dunwiddie et al., Ann. Rev. Neuroscience 24:31-55 (2001).

SUMMARY OF THE INVENTION

The invention is based on the discovery that compounds of formula (I) are unexpectedly potent antagonists of the $A_{2a}$ subtype of adenosine receptors. Many compounds of formula (I) also selectively inhibit the $A_{2a}$ adenosine receptors. Adenosine antagonists of the present invention are useful in the prevention and/or treatment of various diseases and disorders related to modulation of $A_{2a}$ adenosine receptor signaling pathways. Such a disease or disorder can be, e.g., neurodegenerative diseases such as Parkinson's disease and Parkinson's-like syndromes such as progressive supranuclear palsy and multiple system atrophy, senile dementia such as Alzheimer's disease, depression, AIDS encephalopathy, multiple sclerosis, amyotrophic lateral sclerosis, migraine, attention deficit disorder, narcolepsy, sleep apnea or other disorders that cause excessive daytime sleepiness, Huntington's disease, cerebral ischemia, brain trauma, hepatic fibrosis, cirrhosis, and fatty liver.

In one aspect, the invention features compounds of formula (I):

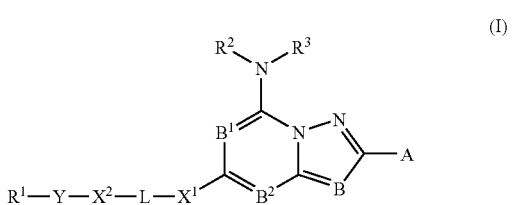

(I)

A can be an aryl or heteroaryl. Each of B, $B^1$, and $B^2$, independently, can be N or $CR^2$; provided that at least one of $B^1$ and $B^2$ is N. Each of $R^2$ and $R^3$, independently, can be hydrogen, alkyl, cycloalkyl, cycloalkenyl, aryl, aralkyl, heterocycloalkyl, heterocycloalkenyl, heteroaryl, or heteroaralkyl. $X^1$ can be a bond or $C_{1-6}$ alkylene, $C_{2-6}$ alkenylene, or $C_{2-6}$ alkynylene, and each of the $C_{1-6}$ alkylene, $C_{2-6}$ alkenylene, and $C_{2-6}$ alkynylene can be optionally interrupted by or linked terminally to —O—, —S—, or —N($R^2$)—. For example, $X^1$ can be a propylene that is interrupted by —O— (e.g., —CH$_2$—CH$_2$—O—CH$_2$—) or $X^1$ can be an ethylene that is linked terminally to —NH— (e.g., —CH$_2$—CH$_2$—NH— or —NH—CH$_2$—CH$_2$—). $X^2$ is a bond, $C_{1-6}$ alkylene, $C_{2-6}$ alkenylene, or $C_{2-6}$ alkynylene. Y is —C($R^2$)($R^3$)—, —N(R''')—, —O—, —S—, —SO—, —SO$_2$—, —CO—, —CO$_2$—, or a bond where R''' is hydrogen, alkyl, alkenyl, alkynyl, cycloalkyl, cycloalkylalkyl, cycloalkenyl, cycloalkenylalkyl, aryl, aralkyl, heterocyclyl, or heterocyclylalkyl. $R^1$ is hydrogen, alkyl, alkenyl, alkynyl, cycloalkyl, cycloalkylalkyl, cycloalkenyl, cycloalkenylalkyl, aryl, aralkyl, heterocyclyl, or heterocyclylalkyl. L is a linker selected from the group consisting of:

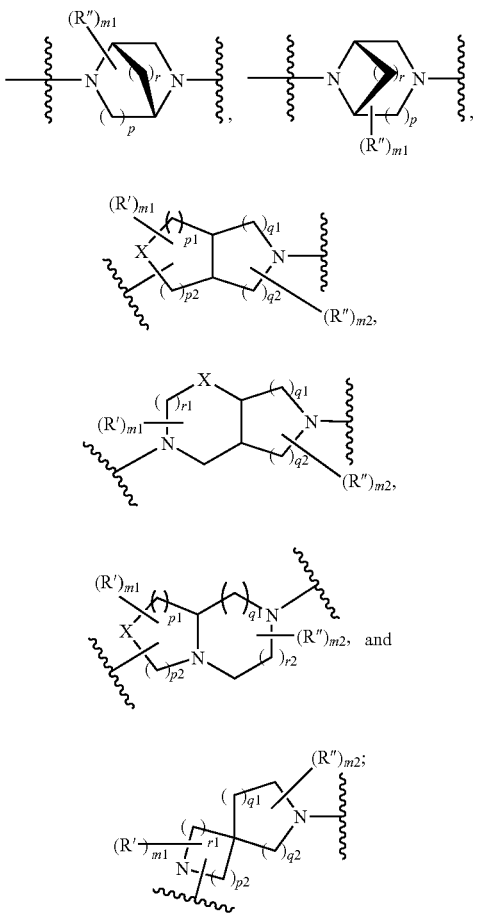

wherein each of R' and R'', independently, can be hydrogen, alkyl, alkenyl, alkynyl, alkoxy, acyl, halo, hydroxy, amino, nitro, oxo, thioxo, cyano, guanadino, amidino, carboxy, sulfo, sulfoxy, mercapto, alkylsulfanyl, alkylsulfinyl, alkylsulfonyl, aminocarbonyl, alkylcarbonylamino, alkylsulfonylamino, alkoxycarbonyl, alkylcarbonyloxy, urea, thiourea, sulfamoyl, sulfamide, carbamoyl, cycloalkyl, cycloalkyloxy, cycloalkylsulfanyl, heterocycloalkyl, heterocycloalkyloxy, heterocycloalkylsulfanyl, aryl, aryloxy, arylsulfanyl, aroyl, heteroaryl, heteroaryloxy, heteroarylsulfanyl, or heteroaroyl; X is —C($R^2$)($R^3$)—, —N($R^2$)—, —O—, or —S— (where each of $R^2$ and $R^3$ has been defined above); each of p1, p2, q1, q2, m1, and m2, independently, can be 0-2; each of r and r1 is independently is 1-2; and r2 is 0-1.

In one embodiment, L can be

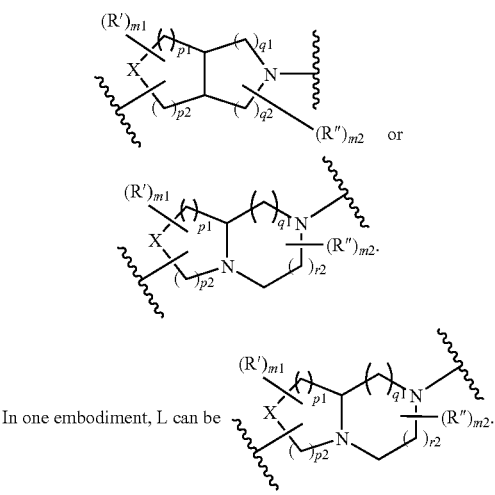

In one embodiment, X is —CH$_2$—, p1 is 1, p2 is 1 or 2, q1 is 1, r2 is 1 or 2, each of m1 and m2 is independently 0 or 1, and each of R' and R" is independently hydrogen or alkyl. For example, L can be

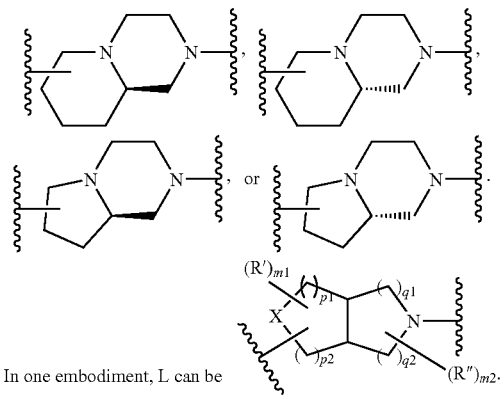

In one embodiment, L can be

In one embodiment, X is —CH$_2$—, p1 is 0 or 1, p2 is 1 or 2, q1 is 1, q2 is 1 or 2, each of m1 and m2 is independently 0 or 1, and each of R' and R" is independently hydrogen or alkyl. For example, L can be

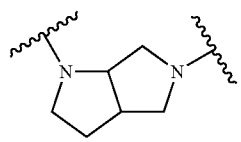

In one embodiment, X$^1$ can be a bond or C$_{1-4}$ alkylene that is optionally linked terminally to —N(R$^2$)—, where R$^2$ is hydrogen or alkyl.

In one embodiment, X$^2$ can be a bond or C$_{1-4}$ alkylene.

In one embodiment, Y can be —N(R''')—, —O—, —S—, or a bond where R''' can be hydrogen, alkyl, cycloalkyl, cycloalkylalkyl, aryl, aralkyl, heterocyclyl, or heterocyclylalkyl. For example, R''' can be hydrogen, cycloalkylalkyl, heterocycloalkylalkyl, aryl, heteroaryl, aralkyl, or heteroaralkyl.

In one embodiment, B can be N.

In one embodiment, each of B$^1$ and B$^2$, independently, can be N or CH.

In one embodiment, each of R$^2$ and R$^3$, independently, can be hydrogen or alkyl.

In one embodiment, R$^1$ is hydrogen, alkyl, cycloalkyl, cycloalkylalkyl, aryl, aralkyl, heterocyclyl, or heterocyclylalkyl. For example, R$^1$ can be hydrogen, or R$^1$ can be phenyl, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, triazinyl, quinolinyl, isoquinolinyl, indolyl, isoindolyl, benzofuryl, benzothiophenyl, benzimidazolyl, benzthiazolyl, furopyridyl, or thienopyridyl; each of these cyclic moieties can be optionally substituted with C$_{1-4}$ alkyl, halo, hydroxy, C$_{1-4}$ alkoxy, or C$_{1-4}$ alkylthio.

In one embodiment, A can be heteroaryl.

In one embodiment, L is (where X can be —CH$_2$—, p1 can be 1, p2 can be 1 or 2, q1 can be 1, r2 can be 1 or 2, each of m1 and m2, independently, can be 0 or 1, and each of R' and R", independently, can be hydrogen or alkyl); X$^1$ is a bond or C$_{1-4}$ alkylene that is optionally linked terminally to —N(R$^2$)—; X$^2$ is a bond or C$_{1-4}$ alkylene; Y is —N(R''')—, —O—, —S—, or a bond where R''' is hydrogen, cycloalkylalkyl, heterocycloalkylalkyl, aryl, heteroaryl, aralkyl, or heteroaralkyl; B is N; each of B$^1$ and B$^2$, independently, is N or CH; each of R$^2$ and R$^3$ is independently hydrogen or alkyl; R$^1$ is cycloalkyl, cycloalkylalkyl, aryl, aralkyl, heterocyclyl, or heterocyclylalkyl; and A is heteroaryl. For example, X$^1$ can be a bond; each of R$^2$ and R$^3$ can be hydrogen; and R$^1$ can be aryl or heteroaryl.

In one embodiment, L is (where X can be —CH$_2$—, p1 can be 0 or 1, p2 can be 1 or 2, q1 can be 1, q2 can be 1 or 2, each of m1 and m2, independently, can be 0 or 1, and each of R' and R" can be independently hydrogen or alkyl); X$^1$ is a bond or C$_{1-4}$ alkylene that is optionally linked terminally to —N(R$^2$)— where R$^2$ is hydrogen or alkyl; X$^2$ is a bond or C$_{1-4}$ alkylene; Y is —N(R''')—, —O—, —S—, or a bond where R''' is hydrogen, cycloalkylalkyl, heterocycloalkylalkyl, aryl, heteroaryl, aralkyl, or heteroaralkyl; B is N; each of B$^1$ and B$^2$, independently, is N or CH; each of R$^2$ and R$^3$ is independently hydrogen or alkyl; R$^1$ is cycloalkyl, cycloalkylalkyl, aryl, aralkyl, heterocyclyl, or heterocyclylalkyl; and A is heteroaryl.

Some examples of a compound of formula (I) are shown in Examples 1-153 below.

An N-oxide derivative or a pharmaceutically acceptable salt of each of the compounds of formula (I) is also within the scope of this invention. For example, a nitrogen ring atom of the triazolotriazine or the pyrazolotriazine core ring or a nitrogen-containing heterocyclyl substituent can form an oxide in the presence of a suitable oxidizing agent such as m-chloroperbenzoic acid or $H_2O_2$.

A compound of formula (I) that is acidic in nature (e.g., having a carboxyl or phenolic hydroxyl group) can form a pharmaceutically acceptable salt such as a sodium, potassium, calcium, or gold salt. Also within the scope of the invention are salts formed with pharmaceutically acceptable amines such as ammonia, alkyl amines, hydroxyalkylamines, and N-methylglycamine. A compound of formula (I) can be treated with an acid to form acid addition salts. Examples of such an acid include hydrochloric acid, hydrobromic acid, hydroiodic acid, sulfuric acid, methanesulfonic acid, phosphoric acid, p-bromophenyl-sulfonic acid, carbonic acid, succinic acid, citric acid, benzoic acid, oxalic acid, malonic acid, salicylic acid, malic acid, fumaric acid, ascorbic acid, maleic acid, acetic acid, and other mineral and organic acids well known to a skilled person in the art. The acid addition salts can be prepared by treating a compound of formula (I) in its free base form with a sufficient amount of an acid (e.g., hydrochloric acid) to produce an acid addition salt (e.g., a hydrochloride salt). The acid addition salt can be converted back to its free base form by treating the salt with a suitable dilute aqueous basic solution (e.g., sodium hydroxide, sodium bicarbonate, potassium carbonate, or ammonia). Compounds of formula (I) can also be, e.g., in a form of achiral compounds, racemic mixtures, optically active compounds, pure diastereomers, or a mixture of diastereomers.

Compounds of formula (I) exhibit surprisingly high affinity to the $A_{2a}$ subtype of adenosine receptors, e.g., with $K_i$ values of less than 10 µM under conditions as described in Example 154. Some compounds of formula (I) exhibit $K_i$ values of below 1 µM. Many compounds of formula (I) are selectively inhibitors of the $A_{2a}$ adenosine receptors (e.g., these compounds inhibit the $A_{2a}$ adenosine receptors at least 10 times better than other subtypes of adenosine receptors, e.g., the $A_1$ adenosine receptors or the $A_3$ adenosine receptors.

Compounds of formula (I) can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom-substitution in aromatic rings.

In another aspect, the present invention features a pharmaceutical composition comprising a compound of formula (I) (or a combination of two or more compounds of formula (I)) and a pharmaceutically acceptable carrier. Also included in the present invention is a medicament composition including any of the compounds of formula (I), alone or in a combination, together with a suitable excipient.

In a further aspect, the invention features a method of inhibiting the $A_{2a}$ adenosine receptors (e.g., with an $K_i$ value of less than 10 µM; preferably, less than 1 µM) in a cell, including the step of contacting the cell with an effective amount of one or more compounds of formula (I). Also with the scope of the invention is a method of modulating the $A_{2a}$ adenosine receptor signaling pathways in a cell or in a subject (e.g., a mammal such as human), including the step of contacting the cell with or administering to the subject an effective amount of one or more of a compound of formula (I).

Also within the scope of the present invention is a method of treating a subject or preventing a subject suffering from a condition or a disease wherein the causes or symptoms of the condition or disease are associated with an activation of the $A_{2a}$ adenosine receptor. The method includes the step of administering to the subject an effective amount of one or more of a compound of formula (I). The conditions or diseases can be, e.g., neurodegenerative diseases such as Parkinson's disease and Parkinson's-like syndromes such as progressive supranuclear palsy and multiple system atrophy, senile dementia such as Alzheimer's disease, depression, AIDS encephalopathy, multiple sclerosis, amyotrophic lateral sclerosis, migraine, attention deficit disorder, narcolepsy, sleep apnea or other disorders that cause excessive daytime sleepiness, Huntington's disease, cerebral ischemia, brain trauma, hepatic fibrosis, cirrhosis, and fatty liver.

Compounds of formula (I) may be utilized as sedatives, muscle relaxants, antipsychotics, antidepressants, anxiolytics, analgesics, respiratory stimulants, antiepileptics, anticonvulsants, and cardioprotective agents.

Also within the scope of the invention is a method of treating or preventing a condition or a disease characterized by or resulted from an over-activation of the $A_{2a}$ adenosine receptor by administering to a subject in need of such a treatment an effective amount of any of compounds of formula (I) in combination with one or more known $A_{2a}$ antagonists. For example, a patient suffering from Parkinson's disease can be treated by administering an effective amount of a compound of formula (I) in combination with an agent such as L-DOPA, a dopaminergic agonist, an inhibitor of monoamine oxidase (type B), a DOPA decarboxylase inhibitor, or a catechol-O-methyltransferase inhibitor. The compound of formula (I) and the agent can be administered to a patient simultaneously or in sequence. The invention also includes a pharmaceutical composition containing one or more of a compound of formula (I), one or more of a known $A_{2a}$ antagoinst, and a suitable excipient.

As used herein, an "alkyl" group refers to a saturated aliphatic hydrocarbon group containing 1-8 (e.g., 1-6 or 1-4) carbon atoms. An alkyl group can be straight or branched. Examples of an alkyl group include, but are not limited to, methyl, ethyl, propyl, isopropyl, butyl, isobutyl, sec-butyl, tert-butyl, n-pentyl, n-heptyl, and 2-ethylhexyl. An alkyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy. An "alkylene" is a divalent alkyl group, as defined herein.

As used herein, an "alkenyl" group refers to an aliphatic carbon group that contains 2-8 (e.g., 2-6 or 2-4) carbon atoms and at least one-double bond. Like an alkyl group, an alkenyl group can be straight or branched. Examples of an alkenyl group include, but are not limited to allyl, isoprenyl, 2-butenyl, and 2-hexenyl. An alkenyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy. An "alkenylene" is a divalent alkenyl group, as defined herein.

As used herein, an "alkynyl" group refers to an aliphatic carbon group that contains 2-8 (e.g., 2-6 or 24) carbon atoms and has at least one triple bond. An alkynyl group can be straight or branched. Examples of an alkynyl group include, but are not limited to, propargyl and butynyl. An alkynyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy. An "alkynylene" is a divalent alkynyl group, as defined herein.

As used herein, an "amino" group refers to —NR$^X$R$^Y$ wherein each of R$^X$ and R$^Y$ is independently hydrogen, alkyl, cycloalkyl, (cycloalkyl)alkyl, aryl, aralkyl, heterocycloalkyl, (heterocycloalkyl)alkyl, heteroaryl, or heteroaralkyl. When the term "amino" is not the terminal group (e.g., alkylcarbonylamino), it is represented by —NR$^X$—. R$^X$ has the same meaning as defined above.

As used herein, an "aryl" group refers to phenyl, naphthyl, or a benzofused group having 2 to 3 rings. For example, a benzofused group includes phenyl fused with one or two $C_{4-8}$ carbocyclic moieties, e.g., 1,2,3,4-tetrahydronaphthyl, indanyl, or fluorenyl. An aryl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl.

As used herein, a "cycloalkyl" group refers to an aliphatic carbocyclic ring of 3-10 (e.g., 4-8) carbon atoms. Examples of cycloalkyl groups include cyclopropyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, and bicyclo[3.2.3]nonyl. A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, bicyclo[2.2.2]octenyl, and bicyclo[3.3.1]nonenyl. A cycloalkyl or cycloalkenyl group can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, a "heterocycloalkyl" group refers to a 3- to 10-membered (e.g., 4- to 8-membered) saturated ring structure, in which one or more of the ring atoms is a heteroatom, e.g., N, O, or S. Examples of a heterocycloalkyl group include piperidinyl, piperazinyl, tetrahydropyranyl, tetrahydrofuryl, dioxolanyl, oxazolidinyl, isooxazolidinyl, morpholinyl, octahydro-benzofuryl, octahydro-chromenyl, octahydro-thiochromenyl, octahydro-indolyl, octahydro-pyrindinyl, decahydro-quinolinyl, octahydro-benzo[b]thiophenyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A "heterocycloalkenyl" group, as used herein, refers to a 3- to 10-membered (e.g., 4- to 8-membered) non-aromatic ring structure having one or more double bonds, and wherein one or more of the ring atoms is a heteroatom, e.g., N, O, or S. A heterocycloalkyl or heterocycloalkenyl group can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

A "heteroaryl" group, as used herein, refers to a monocyclic, bicyclic, or tricyclic ring structure having 5 to 15 ring atoms wherein one or more of the ring atoms is a heteroatom, e.g., N, O, or S and wherein one or more rings of the bicyclic or tricyclic ring structure is aromatic. Some examples of heteroaryl are pyridyl, furyl, pyrrolyl, thienyl, thiazolyl, oxazolyl, imidazolyl, indolyl, tetrazolyl, benzofuryl, benzthiazolyl, xanthene, thioxanthene, phenothiazine, dihydroindole, and benzo[1,3]dioxole. A heteroaryl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl. A "heteroaralkyl" group, as used herein, refers to an alkyl group (e.g., a $C_{1-4}$ alkyl group) that is substituted with a heteroaryl group. Both "alkyl" and "heteroaryl" have been defined above.

As used herein, "heterocyclyl" includes heterocycloalkyl, heterocycloalkenyl, and heteroaryl, each of which has been defined previously.

As used herein, "cyclic moiety" includes cycloalkyl, heterocycloalkyl, cycloalkenyl, heterocycloalkenyl, aryl, and heteroaryl, each of which has been defined previously.

As used herein, an "acyl" group refers to a formyl group or alkyl-C(=O)— where "alkyl" has been defined previously. Acetyl and pivaloyl are examples of acyl groups.

As used herein, a "carbamoyl" group refers to a group having the structure —O—CO—$NR^XR^Y$ or —$NR^X$—CO—O—$R^Z$ wherein $R^X$ and $R^Y$ have been defined above and $R^Z$ is alkyl, cycloalkyl, (cycloalkyl)alkyl, aryl, aralkyl, heterocycloalkyl, (heterocycloalkyl)alkyl, heteroaryl, or heteroaralkyl.

As used herein, a "carboxy" and a "sulfo" group refer to —COOH and —$SO_3H$, respectively.

As used herein, an "alkoxy" group refers to an alkyl-O— group where "alkyl" has been defined previously.

As used herein, a "sulfoxy" group refers to —O—SO—$R^X$ or —SO—O—$R^X$, where $R^X$ has been defined above.

As used herein, a "halogen" or "halo" group refers to fluorine, chlorine, bromine or iodine.

As used herein, a "sulfamoyl" group refers to the structure —$SO_2$—$NR^XR^Y$ or —$NR^X$—$SO_2$—$R^Z$ wherein $R^X$, $R^Y$, and $R^Z$ have been defined above.

As used herein, a "sulfamide" group refers to the structure —$NR^X$—$S(O)_2$—$NR^YR^Z$ wherein $R^X$, $R^Y$, and $R^Z$ have been defined above.

As used herein, a "urea" group refers to the structure —$NR^X$—CO—$NR^YR^Z$ and a "thiourea" group refers to the structure —$NR^X$—CS—$NR^YR^Z$. $R^X$, $R^Y$, and $R^Z$ have been defined above.

As used herein, an effective amount is defined as the amount which is required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

An antagonist is a molecule that binds to the receptor without activating the receptor. It competes with the endogenous ligand(s) or substrate(s) for binding site(s) on the receptor and, thus inhibits the ability of the receptor to transduce an intracellular signal in response to endogenous ligand binding.

As compounds of formula (I) are antagonists of the $A_{2a}$ subtype of the adenosine receptors, these compounds are useful in inhibiting the consequences of signal transduction through the adenosine $A_{2a}$ receptor. Thus, compounds of formula (I) possess the therapeutical utility of treating and/or preventing disorders or diseases for which inhibition of the adenosine $A_{2a}$ receptor signaling pathways is desirable (e.g., Parkinson's disease or depression).

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In addition, the materials, methods, and examples are illustrative only and not intended to be limiting.

Other features and advantages of the invention will be apparent from the following detailed description, and from the claims.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable materials and methods are described below. All publications, patent applications, patents, and other references mentioned herein are incorporated by reference in their entirety. In addition, the materials, methods, and examples are illustrative only and are not intended to be limiting.

Synthesis of the Adenosine Antagonist Compounds

Compounds of formula (I) may be prepared by a number of known methods from commercially available or known starting materials.

In one method, a compound of formula (I) is prepared according to the method outlined in Scheme 1 below. Specifically, the method utilizes a sulfone starting material (II) or a chloro (or other halo groups) starting material (III). The sulfone starting material (II), wherein B, $B^1$, and $B^2$ are N and $X^1$ is a bond, can be prepared according to known methods, e.g., see Caulkett et al., *J. Chem. Soc. Perkin Trans I.* 801-808 (1995) and de Zwart et al., *Drug Dev. Res.* 48:95-103 (1999). The chloro starting material (III) (wherein B is N or C, either $B^1$ or $B^2$ is N, and $X^1$ is a bond) can also be prepared according to known methods, see, e.g., U.S. Pat. No. 6,222,035 and WO 99/43678. See also Kranz, E. et al., Chemische Berichte 105:388-405 (1972) and Marei, M. G., Bulletin of the Chemical Society of Japan 66:1172-1175 (1993). As apparent to a skilled person in the art, starting materials wherein $X^1$ is not a bond (e.g., $X^1$ is an alkynylene) can be prepared by many known methods. For example, one can react the sulfone starting material (II) wherein $X^1$ is a bond (e.g., 2-furan-2-yl-5-methanesulfonyl-[1,2,4]triazolo[1,5-a][1,3,5]triazin-7-ylamine) with an appropriate nucleophile, e.g., methylsulfanylethyne or chloroethyne, to form an intermediate with a methylsulfanyl or a chloro group, respectively. The intermediate with a methylsulfanyl group can be further modified by, e.g., oxidation of the methylsulfanyl group to methylsulfonyl group to form a starting material (II) wherein $X^1$ is an alkynylene.

According to the method depicted in Scheme 1, the starting material (II) or (III) can react with a bicyclic diamine compound L (e.g., 2,5-diaza-bicyclo[2.2.1]heptane) to form an intermediate (IV). The reaction can be carried out in an appropriate solvent such as acetonitrile ($CH_3CN$), dimethyl sulfoxide (DMSO), or N,N-dimethylformamide (DMF) at a temperature ranging from about 80° C. to about 120° C. The intermediate (IV) can further react, via the free amino group of moiety L, with a compound of the formula $R^1$—Y—$X^2$-LG (where $R^1$, Y, and $X^2$ have been defined above and LG represents an appropriate leaving group such as halide, mesylate, or tosylate) to form a desired compound of formula (I). See Route (A) below and Examples 13 and 15.

Alternatively, the intermediate (IV) can react with an appropriate aldehyde or carboxylic acid to form an amide, which can then undergo reductive amination to form a desired compound of formula (I). Examples of a typical reducing agent used in this reaction are sodium cyanoborohydride and sodium triacetoxyborohydride. See Route (B) below and Example 14.

Still another alternative method involves reacting the intermediate (IV) with an appropriate epoxide to form a desired compound of formula (I). See Route (C) below. Note that the reaction between moiety L and the epoxide ring leads to opening of the ring, thus forming a hydroxy-containing moiety $X^2$. Moiety $X^{2a}$ and hydroxyethylene group (from the epoxide ring) together form moiety $X^2$ (see route (C) shown in Scheme 1 below).

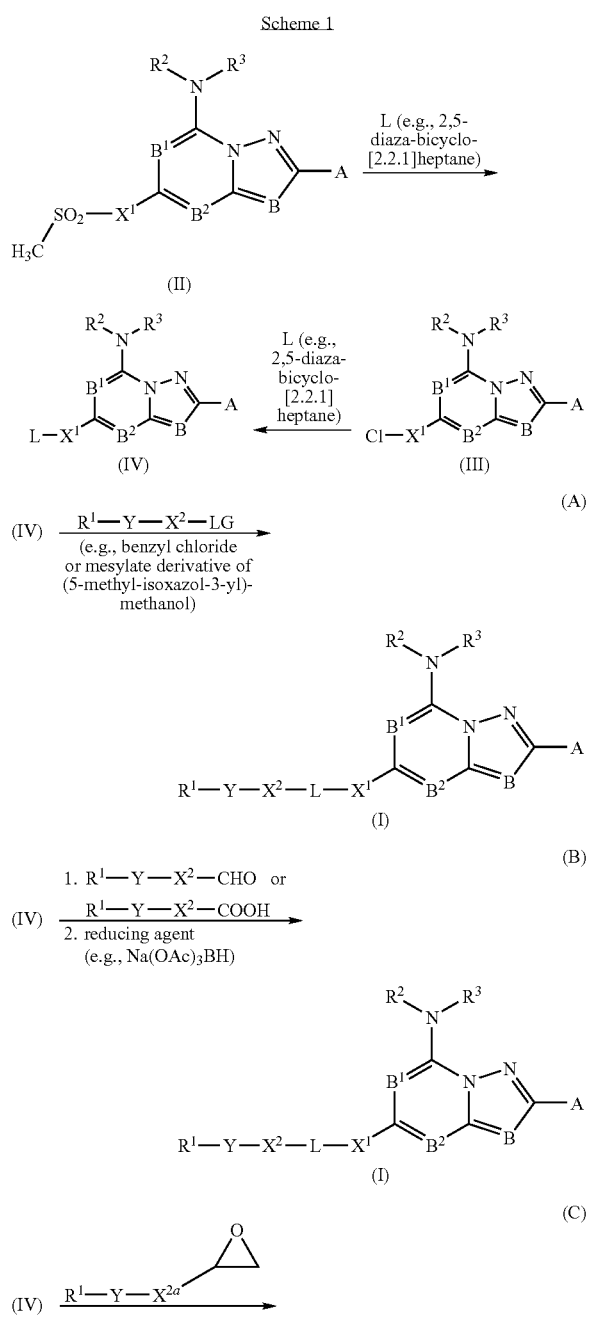

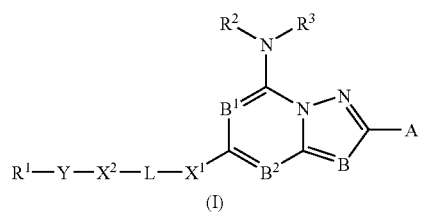

In another method, a compound of formula (I) can be prepared by reacting the starting material of formula (II) or formula (III) with a compound of the formula Y'—$X^2$-L', where L' and Y' are the precursor of moieties L and Y, respectively. For example, the compound Y'—$X^2$-L' can be a hydroxyalkyl substituted bicyclic compound with a nitrogen ring atom (e.g., (octahydro-pyrido[1,2-a]pyrazin-7-yl)-methanol). Note that a compound of the formula Y'—$X^2$-L' can be prepared by known methods, see, e.g., Bright and Desai, U.S. Pat. No. 5,122,525 and Urban, J. Heterocyclic Chem. 32: 857 (1995). The free amine of the bicyclic ring can react with the sulfone or halo group of the starting material (II) or (III) to form the intermediate (V). The hydroxy group of moiety Y' can undergo further modification and then react with a compound $R^{1'}$ (the precursor of moiety $R^1$) to form a compound of formula (I). For example, Y' can be converted from a hydroxyl group to a mesylate or a tosylate group, which can react with a compound $R^{1'}$ (e.g., a phenol or a piperidine) to form a compound of formula (I). See Scheme 2, route (1) below and Example 5. As another example, Y' can be converted from a hydroxyl group to tin amine group, which can undergo further transformations, e.g., according to route (A), (B), or (C) as shown in Scheme 1, to form a compound of formula (I). See Scheme 2, route (2) below and Examples 9-12.

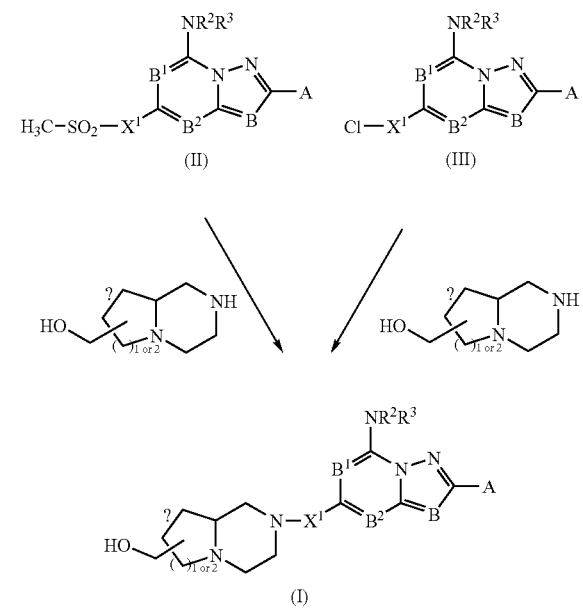

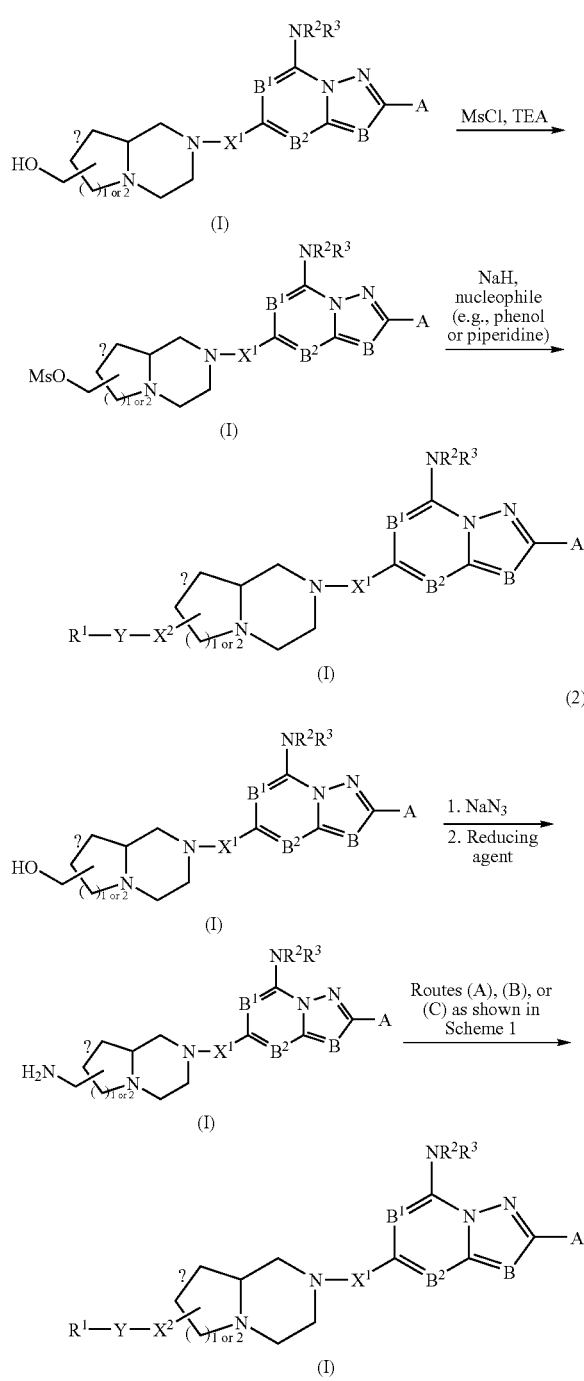

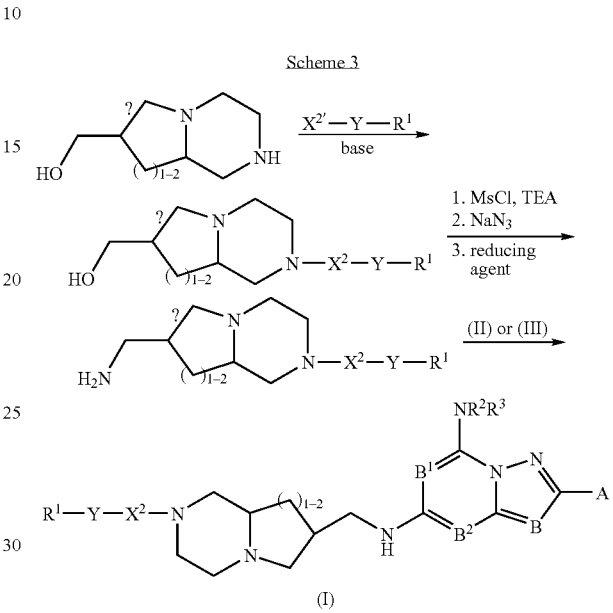

zylbromide) to form a compound of the formula $R^1$—Y—$X^2$-L-$X^{1'}$ (e.g., [2-(2,4-difluoro-benzyl)-octahydro-pyrido[1,2-a]pyrazin-6-yl]-methanol, wherein Y is a bond). This compound of the formula $R^1$—Y—$X^2$-L-$X^{1'}$ can be further modified to convert the hydroxyl group into an amine group (e.g., C-[2-(2,4-difluoro-benzyl)-octahydro-pyrido[1,2-a]pyrazin-6-yl]-methylamine), which can react with a starting material (II) or (III) to yield a compound of formula (I). See Scheme 3 and Example 6 below.

As can be appreciated by the skilled artisan, the above synthetic schemes are exemplary and not intended to comprise a comprehensive list of all means by which the compounds described and claimed in this application may be synthesized. For example, the reaction steps shown in the schemes above can be conducted in a different order, e.g., by reacting a compound of the formula Y—$X^2$-L with the sulfone or chloride starting material before coupling with $R^1$. Further methods will be evident to those of ordinary skill in the art.

For reference on protecting groups, see, e.g., Greene and Wutts: *Protective Groups in Organic Synthesis*, $3^{rd}$ edition, John Wiley & Sons (1999).

Uses for the $A_{2a}$ Adenosine Antagonist Compounds

Compounds of the invention are useful in the prevention and/or treatment of various neurological diseases and disorders whose causes or symptoms are mediated by the $A_{2a}$ adenosine receptor signaling pathways. Such diseases and disorders include Parkinson's disease and related neurodegenerative disorders, depression, anxiety, and cerebrovascular disorders such as migraine. In addition, compositions of the invention are useful for neuroprotection, i.e., to prevent or inhibit neuronal death or degeneration associated with conditions such as Alzheimer's disease, stroke (cerebral ischemia), and brain trauma.

In a further method, the compound of the formula L'-$X^{1'}$ (wherein L' and $X^{1'}$ are precursors of moiety L and $X^1$, respectively) can couple to a compound $R^1$—Y—$X^{2'}$ (wherein $X^{2'}$ is the precursor of moiety $X^2$) to form a compound of the formula $R^1$—Y—$X^2$-L-$X^{1'}$ prior to reacting with a starting material of formula (II) or formula (III). For example, the compound L'-$X^{1'}$ can be a hydroxyalkyl substituted bicyclic compound with a nitrogen ring atom (e.g., (octahydro-pyrido[1,2-a]pyrazin-6-yl)-methanol), which can react with a halo-substituted aralkyl (e.g., 2,4-difluoroben- Administration of Compounds of the Invention Compounds of the invention can be administered to an animal, preferably a mammal, e.g., a human, non-human primate, dog, pig, sheep, goat, cat, mouse, rat, guinea pig, rabbit, hamster, or marmoset. The compounds can be administered in any manner suitable for the administration of pharmaceutical compounds, including, but not limited to, pills, tablets, capsules, aerosols, suppositories, liquid formulations for ingestion or injection or for use as eye or ear drops, dietary supplements, and topical preparations. The compounds can be administered orally, intranasally, transdermally, intradermally, vaginally, intraaurally, intraocularly, buccally, rectally, transmucosally, or via inhalation, implantation (e.g., surgically), or intravenous administration.

Pharmaceutical Compositions

Compounds of the invention can be formulated into pharmaceutical compositions for administration to animals, including humans. These pharmaceutical compositions preferably include a pharmaceutically acceptable carrier and an amount of $A_{2a}$ adenosine receptor antagonist effective to improve neurological functions such as motor functions and cognitive functions.

Pharmaceutically acceptable carriers useful in these pharmaceutical compositions include, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention can be administered parenterally, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention can be aqueous or oleaginous suspension. These suspensions may be formulated according to techniques known in the art using suitable dispersing or wetting agents and suspending agents. The sterile injectable preparation can also be a sterile injectable solution or suspension in a non-toxic parenterally-acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also can contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms also can be used for the purposes of formulation.

Parenteral formulations can be a single bolus dose, an infusion or a loading bolus dose followed with a maintenance dose. These compositions can be administered once a day or on an "as needed" basis.

The pharmaceutical compositions of this invention be administered orally in any orally acceptable dosage form including, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents can also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Topical application can be effected in a rectal suppository formulation (see above) or in a suitable enema formulation. Topically-transdermal patches may also be used.

For topical applications, the pharmaceutical compositions can be formulated in a suitable ointment containing the active component suspended or dissolved in one or more carriers. Carriers for topical administration of the compounds of this invention include, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention also can be administered by nasal aerosol or inhalation. Such compositions can be prepared according to techniques known in the art of pharmaceutical formulation, and can be prepared as solutions in saline, employing benzyl alcohol or other suitable preservatives, absorption promoters to enhance bioavailability, fluorocarbons, and/or other conventional solubilizing or dispersing agents.

The amount of $A_{2a}$ adenosine receptor antagonist that may be combined with the carrier materials to produce a single dosage form will vary depending upon the host treated and the particular mode of administration. The compositions can be formulated so that a dosage of between 0.01-100 mg/kg body weight of the $A_{2a}$ adenosine receptor antagonist is administered to a patient receiving these compositions. In some embodiments of the invention, the dosage is 0.1-10 mg/kg body weight. The composition may be administered as a single dose, multiple doses or over an established period of time in an infusion.

A specific dosage and treatment regimen for any particular patient will depend upon a variety of factors, including the particular $A_{2a}$ adenosine receptor antagonist, the patient's age, body weight, general health, sex, and diet, and the time of administration, rate of excretion, drug combination, and the severity of the particular disease being treated. Judgment of such factors by medical caregivers is within ordinary skill in the art. The amount of antagonist will also depend on the individual patient to be treated, the route of administration, the type of formulation, the characteristics of the compound used, the severity of the disease, and the desired effect. The amounts of antagonist can be determined by pharmacological and pharmacokinetic principles well-known in the art.

The invention will be further described in the following examples, which do not limit the scope of the invention described in the claims.

In the following examples, unless indicated otherwise, all commercial reagents were obtained from Sigma-Aldrich (St. Louis, Mo.), Lancaster (Windham N.H.), Acros (Pittsburgh, Pa.), Alfa (Berkshire, UK), TCI (Portland, Oreg.), or Maybridge (Cornwall, UK).

EXAMPLE 1

(7RS,9aRS)-[2-(7-Amino-2-furan-2-yl-[1,2,4]triazolo[1,5-a][1,3,5]triazin-5-yl)-octahydro-pyrido[1,2-a]pyrazin-7-yl]-methanol 2-Furan-2-yl-5-methanesulfonyl-[1,2,4]triazolo[1,5-a][1,3,5]triazin-7-ylamine (1 eq.; for reference, see *J. Chem. Soc. Perkin Trans.* 1, 801 (1995)) and cis-(octahydro-pyrido[1,2-a]pyrazin-7-yl)-methanol (1-2 eq; see U.S. Pat. No. 5,122,525) were dissolved in DMSO. The mixture was stirred at around 80° C. for 2 hours. The solution was then cooled to room temperature, filtered and purified by preparative HPLC using aqueous $CH_3CN$ solution (buffered with 0.1% TFA) to give the desired compound as a white solid. Alternatively, for scale up synthesis, the DMSO solvent was removed and the crude product was chromatographed on silica gel column using 5-10% $MeOH/CH_2Cl_2$ as eluant to afford the desired product: $^1H$ NMR (400 Hz, $CD_3OD$) δ 7.70 (d, J=2.0 Hz, 1H), 7.12 (d, J=3.5 Hz, 1H), 6.62 (dd, J=3.5, 2.0 Hz, 1H), 4.75 (d, J=12.0 Hz, 1H), 4.65 (d, J=12.5 Hz, 1H), 3.82 (dd, J=10.5, 7.5 Hz, 1H), 3.74 (dd, J=10.5, 7.5 Hz, 1H), 3.11 (dt, J=13.0, 3.0 Hz, 1H), 2.93 (d, J=11.5 Hz, 1H), 2.78 (d, J=11.5 Hz, 1H), 2.68 (dd, J=13.0, 10.5 Hz, 1H), 2.22 (dd, J=11.5, 3.0 Hz, 1H), 2.14 (dt, J=12.0, 3.0 Hz, 1H), 1.93 (m, 1H), 1.85 (brd, J=12.0 Hz, 2H), 1.60 (m, 1H), 1.43 (m, 2H). MS m/z: 371 $[M+H]^+$.

EXAMPLE 2

(6RS,9aRS)-[2-(7-Amino-2-furan-2-yl-[1,2,4]triazolo[1,5-a][1,3,5]triazin-5-yl)-octahydro-pyrido[1,2-a]pyrazin-6-yl]-methanol (6RS,9aRS)-[2-(7-Amino-2-furan-2-yl-[1,2,4]triazolo[1,5-a][1,3,5]triazin-5-yl)-octahydro-pyrido[1,2-a]pyrazin-6-yl]-methanol was prepared in the same manner as described in Example 1, except that cis-(octahydro-pyrido[1,2-a]pyrazin-6-yl)-methanol (see WO 90/08144) was used as the starting material instead of cis-(octahydro-pyrido[1,2-a]pyrazin-7-yl)-methanol. The desired product was obtained as a white solid: $^1H$ NMR (400 Hz, $CD_3OD$) δ 7.75 (d, J=2.0 Hz, 1H), 7.18 (d, J=3.5 Hz, 1H), 6.65 (dd, J=3.5, 2.0 Hz, 1H), 5.08 (brd, J=15.0 Hz, 1H), 4.94 (brd, J=15.0 Hz, 1H), 4.08 (dd, J=12.0, 3.5 Hz, 1H), 3.90 (brd, J=12.0 Hz, 1H), 3.62 (brd, J=12.5 Hz, 1H), 3.36 (m, 2H), 3.16 (m, J=3H), 2.75 (t, J=12.0 Hz, 1H), 1.98 (m, 4H), 1.67 (m, 2H). MS m/z: 371 $[M+H]^+$.

EXAMPLE 3

(7RS,9aRS)-[2-(5-Amino-2-furan-2-yl-[1,2,4]triazolo[1,5-c]pyrimidin-7-yl)-octahydro-pyrido[1,2-a]pyrazin-7-yl]-methanol 7-Chloro-2-furan-2-yl-[1,2,4]triazolo[1,5-c]pyrimidin-5-ylamine (1 eq, see U.S. Pat. No. 6,222,035 B1), cis-(octahydro-pyrido[1,2-a]pyrazin-7-yl)-methanol (1-2 eq.), and CsF (1-2 eq.) were dissolved in DMSO. The mixture was stirred at around 120° C. for 18 hours. The solution was then cooled to room temperature, filtered and purified by preparative HPLC using aqueous $CH_3CN$ (buffered with 0.1% TFA) to give the desired, compound as a white solid. Alternatively, for scale up synthesis, the DMSO solvent was removed and the crude product was chromatographed on silica gel column using 5-10% $MeOH/CH_2Cl_2$ as eluant to afford the desired product: $^1H$ NMR (400 Hz, $CD_3OD$) δ 7.71 (d, J=2.0 Hz, 1H), 7.14 (d, J=3.5 Hz, 1H), 6.63 (dd, J=3.5, 2.0 Hz, 1H), 5.99 (s, 1H), 4.26 (d, J=13.5 Hz, 1H), 4.19 (d, J=13.5 Hz, 1H), 3.83 (dd, J=10.5, 7.5 Hz, 1H), 3.74 (dd, J=10.5, 7.5 Hz, 1H), 3.04 (dt, J=12.5, 3.0 Hz, 1H), 2.95 (d, J=12.0 Hz, 1H), 2.80 (d, J=11.0 Hz, 1H), 2.62 (dd, J=12.5, 10.5 Hz, 1H), 2.22 (m, 2H), 1.98 (m, 1H), 1.86 (brd, 12.0 Hz, 2H), 1.62 (m, 1H), 1.50-1.42 (m, 2H). MS m/z: 370 $[M+H]^+$.

EXAMPLE 4

(7RS,9aRS)-[2-(7-Amino-2-furan-2-yl-[1,2,4]triazolo[1,5-a]pyrimidin-5-yl)-octahydro-pyrido[1,2-a]pyrazin-7-yl]-methanol 5-chloro-2-furan-2-yl-[1,2,4]triazolo[1,5-a]pyrimidin-7-ylamine (1 eq; see WO 99/43678 A1), cis-(octahydro-pyrido[1,2-a]pyrazin-7-yl)-methanol (1-2 eq), and CsF (1-2 eq) were dissolved in DMSO. The mixture was stirred at around 100° C. for 18 hours. The solution was then cooled to room temperature, filtered, and purified by preparative HPLC using aqueous $CH_3CN$ (buffered with 0.1% TFA) to give the desired compound as a white solid. Alternatively, for scale up synthesis, the DMSO solvent was removed and the crude product was chromatographed on silica gel column using 5-10% $MeOH/CH_2Cl_2$ as eluant to afford the desired product: $^1H$ NMR (400 Hz, $CD_3OD$) δ 7.69 (d, J=2.3 Hz, 1H), 7.10 (d, J=3.5 Hz, 1H), 6.61 (dd, J=3.5, 2.3 Hz, 1H), 5.73 (s, 1H), 4.32 (d, J=13.5 Hz, 1H), 4.24 (d, J=13.5 Hz, 1H), 3.82 (dd, J=10.5, 7.5 Hz, 1H), 3.74 (dd, J=10.5, 7.5 Hz, 1H), 3.10 (dt, J=12.5, 3.2 Hz, 1H), 2.94 (d, J=11.5 Hz, 1H), 2.79 (d, J=11.5 Hz, 1H), 2.67 (dd, J=13.0, 10.5 Hz, 1H), 2.21 (m, 2H), 1.96 (m, 1H), 1.85 (brd, 12.0 Hz, 2H), 1.60 (m, 1H), 1.47 (m, 2H). MS m/z: 370 $[M+H]^+$.

EXAMPLE 5

(7RS,9aSR)-5-[7-(3-Fluoro-phenoxymethyl)-octahydro-pyrido[1,2-a]pyrazin-2-yl]-2-furan-2-yl-[1,2,4]triazolo[1,5-a][1,3,5]triazin-7-ylamine Synthesis of the title compound is described in parts (a) and (b) below.

(a) Methanesulfonic acid 2-(7-amino-2-furan-2-yl-[1,2,4]triazolo[1,5-a][1,3,5]triazin-5-yl)-octahydro-pyrido[1,2-a]pyrazin-7-ylmethyl ester A solution containing (7RS,9aSR)-[2-(7-amino-2-furan-2-yl-[1,2,4]triazolo[1,5-a][1,3,5]triazin-5-yl)-octahydro-pyrido[1,2-a]pyrazin-7-yl]-methanol (1 eq.; see Example 1 above) and triethyl amine (4 eq.) in DMF was treated with methansulfonyl chloride (2 eq.) at around 0° C. After 2 hours, the reaction was quenched with ice, treated with 1M NaOH, and the mixture was extracted with methylene chloride. The combined organic layers was washed with brine, dried over $Na_2SO_4$, filtered, and concentrated to give the corresponding mesylate, which was used in the next step without further purification.

(b) (7RS,9aSR)-5-[7-(2-Fluoro-phenoxymethyl)-octahydro-pyrido[1,2-a]pyrazin-2-yl]-2-furan-2-yl-[1,2,4]triazolo[1,5-a][1,3,5]triazin-7-ylamine A solution containing 3-fluorophenol (1.5 eq.) in DMF was treated with sodium hydride (60% oil dispersion, 4 eq.) for 2 hours at around 50° C. A solution containing containing methanesulfonic acid 2-(7-amino-2-furan-2-yl-[1,2,4]triazolo[1,5-a][1,3,5]triazin-5-yl)-octahydro-pyrido[1,2-a]pyrazin-7-ylmethyl ester (1 eq., see subpart (a) above) in DMF was added. The resulting mixture was then heated at around 100° C. for 24 hours. The solvent was removed, and the residue was dissolved in DMSO, filtered and purified by preparative HPLC using aqueous $CH_3CN$ (buffered with 0.1% TFA) to afford the desired product as a white powder: $^1H$ NMR (400 Hz, DMSO-d6) δ 7.96 (d, J=2.0 Hz, 1H), 7.39 (m, 1H), 7.15 (d, J=3.0 Hz, 1H), 6.92-6.83 (m, 3H), 6.75 (dd, J=3.0, 2.0 Hz, 1H), 4.84 (m, 2H), 4.08 (dd, J=10.0, 5.0 Hz, 1H), 3.74 (dd, J=10.0, 7.0 Hz, 1H), 3.65 (m, 2H), 3.33 (m, 3H), 3.10 (m, 1H), 2.97 (m, 1H), 2.39 (m, 1H), 1.99 (m, 2H), 1.67 (m, 1H), 1.48 (m, 1H). MS m/z: 465 [M+H]$^+$.

EXAMPLE 6

(7RS,9aRS)-2-Furan-2-yl-$N^5$-(2-pyrimidin-2-yl-octahydro-pyrido[1,2-a]pyrazin-7-ylmethyl)-[1,2,4]triazolo[1,5-a][1,3,5]triazine-5,7-diamine Synthesis of the title compound is described in parts (a)-(d) below.

(a) Cis-(2-pyrimidin-2-yl-octahydro-pyrido[1,2-a]pyrazin-7-yl)-methanol

Cis-(octahydro-pyrido[1,2-a]pyrazin-7-yl)-methanol (1 eq), 2-chloro-pyrimidine (1 eq.), and $Na_2CO_3$ (1 eq.) were dissolved in water. The mixture was stirred at around 95° C. for overnight. The solution was cooled to room temperature and extracted with methylene chloride. The combined organic layers was washed with brine, dried over $Na_2SO_4$, filtered and concentrated to give cis-(2-pyrimidin-2-yl-octahydro-pyrido[1,2-a]pyrazin-7-yl)-methanol as a white solid. This material was used in the next step without further purification.

(b) Methanesulfonic acid 2-pyrimidin-2-yl-octahydro-pyrido[1,2-a]pyrazin-7-ylmethyl ester A solution of cis-(2-pyrimidin-2-yl-octahydro-pyrido[1,2-a]pyrazin-7-yl)-methanol (1 eq., see subpart (a) above) and triethyl amine (2 eq.) in $CH_2Cl_2$ was treated with methansulfonyl chloride (1.5 eq.) at around 0° C. for 20 minutes. The reaction was quenched with aqueous $Na_2CO_3$ solution (2 M), and the mixture was extracted with methylene chloride. The combined organic layers was washed with brine, dried over $Na_2SO_4$, filtered and concentrated to give the corresponding mesylate as yellow oil. This material was used in the next step without further purification.

(c) 7-Azidomethyl-2-pyrimidin-2-yl-octahydro-pyrido[1,2-a]pyrazine

A solution containing methanesulfonic acid 2-pyrimidin-2-yl-octahydro-pyrido[1,2-a]pyrazin-7-ylmethyl ester (1 eq., see subpart (b) above) and sodium azide (2 eq.) in DMF was stirred at around 90° C. for 24 hours. The solution was cooled to room temperature, diluted with water, and extracted with methylene chloride. The combined organic layers was washed with brine, dried over $Na_2SO_4$, filtered, and concentrated to give the corresponding azide as yellow oil. This material was used in the next step without further purification.

(d) (7RS,9aSR)-2-Furan-2-yl-$N^5$-(2-pyrimidin-2-yl-octahydro-pyrido[1,2-a]pyrazin-7-ylmethyl)-[1,2,4]triazolo[1,5-a]pyrimidine-5,7-diamine A suspension of the azide (1 eq., see subpart (c) above) and polymer supported $PPh_3$ (4 eq., 3 mmol/g loading) in THF was shaken at room temperature for overnight. Water was then added, and the resulting mixture was shaken at room temperature for 2 hours. The suspension was filtered, and the filtered cake was washed with THF and water. The filtrate was lyophilized to give the corresponding amine as yellow oil. This material was coupled, without further purification, to 2-furan-2-yl-5-methanesulfonyl-[1,2,4]triazolo[1,5-a][1,3,5]triazin-7-ylamine in accordance with Example 1 to afford the desired compound: $^1H$ NMR (400 Hz, DMSO-d6) δ 8.52 (d, J=5.0 Hz, 1H), 7.94 (brs, 1H), 7.10 (d, J=3.0 Hz, 1H), 6.84 (t, J=5.0 Hz, 1H), 6.75 (dd, J=3.0, 1.0 Hz, 1H), 4.84 (m, 2H), 3.64-3.19 (m, 8H), 3.13 (m, 1H), 2.30 (m, 1H), 1.88 (m, 2H), 1.80 (m, 2H). MS m/z: 447 [M+H]$^+$.

EXAMPLE 7

(7RS,9aSR)—$N^5$-[2-(5-Chloro-1-methyl-3-trifluoromethyl-1H-pyrazol-4-ylmethyl)-octahydro-pyrido[1,2-a]pyrazin-7-ylmethyl]-2-furan-2-yl-[1,2,4]triazolo[1,5-a][1,3,5]triazine-5,7-diamine Synthesis of the title compound is described in parts (a)-(c) below.

(a) Trans-7-Hydroxymethyl-octahydro-pyrido[1,2-a]pyrazine-2-carboxylic acid tert-butyl ester To a solution of trans-(octahydro-pyrido[1,2-a]pyrazin-7-yl)-methanol (1 eq) in 1,4-dioxane was added aqueous KOH solution (5 N) until the pH value reached 9. A solution of $Boc_2O$ (2 eq.) in 1,4-dioxane was then added. The mixture was stirred at room temperature for overnight, after which the solvent was removed, and the residue was diluted with water, and extracted with methylene chloride. The combined organic phases were washed with brine, dried over $Na_2SO_4$, filtered and concentrated to afford 7-hydroxymethyl-octahydro-pyrido[1,2-a]pyrazine-2-carboxylic acid tert-butyl ester as a white solid. This material was used in the next step without further purification.

(b) Trans-7-[(7-amino-2-furan-2-yl-[1,2,4]triazolo[1,5-a][1,3,5]triazin-5-ylamino)-methyl]-octahydro-pyrido[1,2-a]pyrazine-2-carboxylic acid tert-butyl ester 7-Hydroxymethyl-octahydro-pyrido[1,2-a]pyrazine-2-carboxylic acid tert-butyl ester (see subpart (a) above), was converted to the corresponding mesylate, azide and amine sequentially according to Example 6, subparts (b)-(d) above. The corresponding amine was coupled to 2-furan-2-yl-5-methanesulfonyl-[1,2,4]triazolo[1,5-a][1,3,5]triazin-7-ylamine in accordance to Example 1 to afford trans-7-[(7-amino-2-furan-2-yl-[1,2,4]triazolo[1,5-a][1,3,5]triazin-5-ylamino)-methyl]-octahydro-pyrido[1,2-a]pyrazine-2-carboxylic acid tert-butyl ester as yellow oil. This material was used in the next step without further purification.

(c) (7RS,9aSR)—N$^5$-[2-(5-Chloro-1-methyl-3-trifluoromethyl-1H-pyrazol-4-ylmethyl)-octahydro-pyrido[1,2-a]pyrazin-7-ylmethyl]-2-furan-2-yl-[1,2,4]triazolo[1,5-a][1,3,5]triazine-5,7-diamine To a solution of trans-7-[(7-amino-2-furan-2-yl-[1,2,4]triazolo[1,5-a][1,3,5]triazin-5-ylamino)-methyl]-octahydro-pyrido[1,2-a]pyrazine-2-carboxylic acid tert-butyl ester (1 eq., see subpart (b) above) in methylene chloride was added trifluoroacetic acid to reach a final concentration of 10% TFA. The mixture was stirred at room temperature for 2 hours, after which the solvent was removed under reduced pressure, and the residue was dissolved in methylene chloride. To this solution was added 5-chloro-1-methyl-3-trifluoromethyl-1H-pyrazolen-4-carbaldehyde (1 eq.), sodium triacetoxyborohydride (1.5 eq.), and acetic acid (1.5 eq.). The reaction was stirred at room temperature for overnight. The solvent was then removed, and the residue was purified by preparative HPLC using aqueous CH$_3$CN (buffered with 0.1% TFA) to afford (7RS,9aSR)—N5-[2-(5-Chloro-1-methyl-3-trifluoromethyl-1H-pyrazol-4-ylmethyl)-octahydro-pyrido[1,2-a]pyrazin-7-ylmethyl]-2-furan-2-yl-[1,2,4]triazolo[1,5-a][1,3,5]triazine-5,7-diamine. $^1$H NMR (400 MHz, DMSO-d$_6$) δ 7.70 (d, J=5.0 Hz, 1H), 7.12 (d, J=3.6 Hz, 1H), 6.62 (m, 1H), 4.51 (s, 3H), 4.50 (s, 2H), 3.39-3.53 (m, 4H), 3.00-3.12 (m, 4H), 2.80-2.86 (m, 1H), 2.37-2.43 (m, 1H), 2.21-2.27 (m, 2H), 1.94-1.97 (m, 2H), 1.53-1.58 (m, 1H), 1.30-1.44 (m, 1H). MS m/z=568 (M$^+$+H).

EXAMPLE 8

(7RS,9aSR)-2-Furan-2-yl-N$^5$-(2-pyrimidin-2-yl-octahydro-pyrido[1,2-a]pyrazin-7-ylmethyl)-[1,2,4]triazolo[1,5-a][1,3,5]triazine-5,7-diamine To a solution of trans-7-[(7-amino-2-furan-2-yl-[1,2,4]triazolo[1,5-a][1,3,5]triazin-5-ylamino)-methyl]-octahydro-pyrido[1,2-a]pyrazine-2-carboxylic acid tert-butyl ester (1 eq., see Example 7(b) above) in methylene chloride was added trifluoroacetic acid to reach a final concentration of 10% TFA. The mixture was stirred at room temperature for 2 hours, after which the solvent was removed under reduced pressure, and the residue was dissolved in acetonitrile. To the resulting solution was added 2-chloropyrimidine (1 eq.) and Na$_2$CO$_3$ (2 eq.). The mixture was stirred at around 80° C. for overnight. The solvent was removed afterwards, and the residue was purified by preparative HPLC using aqueous CH$_3$CN (buffered with 0.1% TFA) to afford (7RS,9aSR)-2-furan-2-yl-N$^5$-(2-pyrimidin-2-yl-octahydro-pyrido[1,2-a]pyrazin-7-ylmethyl)-[1,2,4]triazolo[1,5-a][1,3,5]triazine-5,7-diamine. $^1$H NMR (400 MHz, DMSO-d6) δ 8.39 (d, J=4.7 Hz, 2H), 7.70 (d, J=2 Hz, 1H), 7.12 (d, J=3.6 Hz, 1H), 6.72 (t, J=4.7 Hz, 1H), 6.62 (dd, J=2, 3.6 Hz, 1H), 4.97 (d, J=14.1 Hz, 2H), 3.34-3.58 (m, 4H), 3.11-3.24 (m, 3H), 2.82-3.03 (m, 2H), 2.33 (m, 1H), 2.10 (d, J=14.1 Hz, 1H), 2.02 (d, J=13.2 Hz, 1H), 1.60-1.69 (m, 1H), 1.39-1.49 (m, 1H). MS m/z: 448[M+H]$^+$.

EXAMPLE 9

(7RS,9aRS)-5-(7-Aminomethyl-octahydro-pyrido[1,2-a]pyrazin-2-yl)-2-furan-2-yl-[1,2,4]triazolo[1,5-a][1,3,5]triazin-7-ylamine A solution of (7RS,9aRS)-[2-(7-amino-2-furan-2-yl-[1,2,4]triazolo[1,5-a][1,3,5]triazin-5-yl)-octahydro-pyrido[1,2-a]pyrazin-7-yl]-methanol (1 eq.; see Example 1 above) and triethyl amine (2 eq.) in DMF was treated with methansulfonyl chloride (2 eq.) at around 0° C. for 30 minutes. The reaction was then warmed to room temperature. To the reaction solution was added sodium azide (5 eq), and the resulting mixture was stirred at around 100° C. for 24 hours. The solvent was then removed, and the residue was purified by silica gel column chromatography using 5% MeOH/CH$_2$Cl$_2$ to afford the corresponding azide. The azide (1.5 mmol) was subsequently reduced to the corresponding amine in accordance to Example 6(d). The amine was then purified by preparative HPLC using aqueous CH$_3$CN (buffered with 0.1% TFA) to afford (7RS,9aRS)-5-(7-aminomethyl-octahydro-pyrido[1,2-a]pyrazin-2-yl)-2-furan-2-yl-[1,2,4]triazolo[1,5-a][1,3,5]triazin-7-ylamine as a white powder: $^1$H NMR (400 MHz, DMSO-d$_6$) δ 1.68-2.28 (m, 4H); 2.30 (m, 1H); 3.13-3.69 (m, 9H), 4.67-4.79 (m, 2H); 6.69 (dd, J=1.8, 3.4 Hz, 1H); 7.07 (d, J=3.4 Hz); 7.88 (d, J=1.8 Hz), 7.97 (m, 3H); 8.49 (m, 2H). MS m/z: 370 [M+H]$^+$.

EXAMPLE 10

(7RS,9aRS)-5-{7-[(Bis-pyridin-4-ylmethyl-amino)-methyl]-octahydro-pyrido[1,2-a]pyrazin-2-yl}-2-furan-2-yl-[1,2,4]triazolo[1,5-a][1,3,5]triazin-7-ylamine A solution of (7RS,9aRS)-5-(7-aminomethyl-octahydro-pyrido[1,2-a]pyrazin-2-yl)-2-furan-2-yl-[1,2,4]triazolo[1,5-a][1,3,5]triazin-7-ylamine (1 eq.; see Example 9 above) and pyridine-4-carbaldehyde (3 eq.) in dichloroethene was treated with sodium triacetoxyborohydride (3 eq.) and AcOH (3 eq.). The mixture was shaken at room temperature for 24 hours. The solvent was then removed, and the residue was purified by preparative HPLC using aqueous CH$_3$CN (buffered with 0.1% TFA) to afford (7RS,9aRS)-5-{7-[(bis-pyridin-4-ylmethyl-amino)-methyl]-octahydro-pyrido[1,2-a]pyrazin-2-yl}-2-furan-2-yl-[1,2,4]triazolo[1,5-a][1,3,5]triazin-7-ylamine as a white powder: $^1$H NMR (400 MHz, DMSO-d$_6$) δ 1.01-1.32 (m, 1H), 1.50-2.49 (m, 4H), 2.55-3.45 (m, 9H), 3.57-4.03 (m, 4H), 4.55-4.79 (m, 2H), 6.70 (dd, J=1.8, 3.3 Hz, 1H), 7.08 (d, J=3.3 Hz, 1H), 7.76 (d, J=4.5 Hz, 4H), 7.89 (d, J=1.8 Hz, 1H), 8.43-8.62 (m, 2H), 8.73 (d, J=4.5 Hz, 4H). MS m/z: 552 [M+H]$^+$.

EXAMPLE 11

(7RS,9aRS)-2-Furan-2-yl-5-[7-(pyrimidin-2-ylaminomethyl)-octahydro-pyrido[1,2-a]pyrazin-2-yl]-[1,2,4]triazolo[1,5-a][1,3,5]triazin-7-ylamine A solution of (7RS,9aRS)—S-(7-aminomethyl-octahydro-pyrido[1,2-a]pyrazin-2-yl)-2-furan-2-yl-[1,2,4]triazolo[1,5-a][1,3,5]triazin-7-ylamine (1 eq.; see Example 9 above) and 2-chloropyrimidine (2 eq.) in DMSO was treated with K$_2$CO$_3$ (2 eq.). The mixture was stirred at around 85° C. for 4 hours. The reaction mixture was then filtered, and the filtrate was concentrated and purified by preparative HPLC using aqueous CH₃CN (buffered with 0.1% TFA) to afford (7RS, 9aRS)-2-furan-2-yl-5-[7-(pyrimidin-2-ylaminomethyl)-octahydro-pyrido[1,2-a]pyrazin-2-yl]-[1,2,4]triazolo[1,5-a][1,3,5]triazin-7-ylamine as a white powder: $^1$H NMR (400 MHz, DMSO-d₆) δ 1.60-1.86 (m, 4H), 2.21-2.30 (bs, 1H), 3.05-3.32 (m, 4H), 3.33-3.52 (m, 4H), 3.56-3.72 (m, 1H), 4.62-4.83 (m, 2H), 6.63 (t, J=4.8 Hz, 1H), 6.69 (dd, J=1.8, 3.4 Hz, 1H), 7.08 (d, J=3.4 Hz, 1H), 7.41 (t, J=5.6 Hz, 1H), 7.89 (d, J=1.8 Hz, 1H), 8.32 (d, J=4.8 Hz, 2H), 8.40-8.65 (m, 2H). MS m/z: 448 [M+H]⁺.

EXAMPLE 12

(7RS,9aRS)-2-Furan-2-yl-5-(7-{[(pyridin-4-ylmethyl)-amino]-methyl}-octahydro-pyrido[1,2-a]pyrazin-2-yl)-[1,2,4]triazolo[1,5-a][1,3,5]triazin-7-ylamine A solution of (7RS,9aRS)-5-(7-aminomethyl-octahydro-pyrido[1,2-a]pyrazin-2-yl)-2-furan-2-yl-[1,2,4]triazolo[1,5-a][1,3,5]triazin-7-ylamine (1 eq.; see Example 9 above) and pyridine-4-carbaldehyde (1 eq.) in anhydrous THF was treated with titanium (IV) isopropoxide (1.7 eq.) at around 60° C. for 5 hours. To the mixture was added anhydrous methanol, and followed by the careful addition of NaBH₄ (1.5 eq). After one hour, the reaction was completed as indicated by HPLC analysis. The solvent was removed and the residue was purified by preparative HPLC using aqueous CH₃CN (buffered with 0.1% TFA) to afford (7RS,9aRS)-2-furan-2-yl-5-(7-{[(pyridin-4-ylmethyl)-amino]-methyl}-octahydro-pyrido[1,2-a]pyrazin-2-yl)-[1,2,4]triazolo[1,5-a][1,3,5]triazin-7-ylamine as a white powder: $^1$H NMR (400 MHz, CD₃OD) δ 1.77-2.11 (m, 4H), 2.66 (m, 1H), 3.78-3.05 (m, 1H), 4.46 (bs, 2H), 6.65 (dd, J=1.8, 3.4 Hz, 1H), 7.18 (d, J=3.4 Hz, 1H), 7.74 (d, J=1.8 Hz, 1H), 7.88 (d, J=6.0 Hz, 2H), 8.81 (d, J=6.0 Hz, 2H). MS m/z: 461 [M+H]⁺.

EXAMPLE 13

2-Furan-2-yl-5-[5-(5-methyl-isoxazol-3-ylmethyl)-2,5-diaza-bicyclo[2.2.1]hept-2-yl]-[1,2,4]triazolo[1,5-a][1,3,5]triazin-7-ylamine Synthesis of the title compound is described in parts (a)-(b) below.

(a) 5-(2,5-Diaza-bicyclo[2.2.1]hept-2-yl)-2-furan-2-yl-[1,2,4]triazolo[1,5-a][1,3,5]triazin-7-ylamine 2-Furan-2-yl-5-methanesulfonyl-[1,2,4]triazolo[1,5-a][1,3,5]triazin-7-ylamine (0.7 mmol, 1 eq.; see *J. Chem. Soc. Perkin Trans.* 1, 801 (1995)) and 2,5-diaza-bicyclo[2.2.1] heptane (5 eq.) were suspended in 10 mL of CH₃CN. The mixture was stirred under reflux for 2 hours. It was then cooled to room temperature and concentrated under reduced pressure. The residue was taken up in CH₂Cl₂ and washed with water, brine, dried with Na₂SO₄, and concentrated under reduced pressure. The resulting crude product was purified by column chromatography (95% CH₂Cl₂, 4% MEOH, 1% Et₃N) to afford 5-(2,5-diaza-bicyclo[2.2.1]hept-2-yl)-2-furan-2-yl-[1,2,4]triazolo[1,5-a][1,3,5]triazin-7-ylamine.

(b) 2-Furan-2-yl-5-[5-(5-methyl-isoxazol-3-ylmethyl)-2,5-diaza-bicyclo[2.2.1]hept-2-yl]-[1,2,4]triazolo[1,5-a][1,3,5]triazin-7-ylamine In a separate flask, (5-methyl-isoxazol-3-yl)-methanol (32 mg, 0.28 mmol) was dissolved in 4 mL of CH₂Cl₂ along with 1.3 eq. of Et₃N. The solution was cooled in an ice bath and methanesulfonyl chloride (1.2 eq) was added. The reaction mixture was warmed to room temperature and stirred for 45 minutes. It was then quenched with brine and the two layers were separated. The organic layer was dried with Na₂SO₄ and concentrated under reduced pressure to afford the mesylated derivative. This mesylate was then added to a solution containing 5-(2,5-diaza-bicyclo[2.2.1]hept-2-yl)-2-furan-2-yl-[1,2,4]triazolo[1,5-a][1,3,5]triazin-7-ylamine (0.14 mmol; see subpart (a) above), and Et₃N (0.3 mmol) in 3 mL of CH₃CN. The resulting reaction mixture was stirred at room temperature for 18 hours. It was then concentrated and purified by preparative HPLC to afford 2-furan-2-yl-5-[5-(5-methyl-isoxazol-3-ylmethyl)-2,5-diaza-bicyclo[2.2.1]hept-2-yl]-[1,2,4]triazolo[1,5-a][1,3,5]triazin-7-ylamine. $^1$H NMR (400 Hz, DMSO-d₆) δ 8.20 (brs, 1H), 7.80 (d, J=1.0 Hz, 1H), 7.00 (d, J=3.6 Hz, 1H), 6.60 (dd, J=3.6, 1.0 Hz, 1H), 6.30 (s, 1H), 4.80 (brs, 2H), 4.20-4.30 (m, 8H), 2.35 (s, 3H), 2.30 (m, 1H). MS m/z: 394 [M+H]⁺.

EXAMPLE 14

5-[5-(4-Fluoro-benzyl)-2,5-diaza-bicyclo[2.2.1]hept-2-yl]-2-furan-2-yl-[1,2,4]triazolo[1,5-a][1,3,5]triazin-7-ylamine 5-(2,5-Diaza-bicyclo[2.2.1]hept-2-yl)-2-furan-2-yl-[1,2,4]triazolo[1,5-a][1,3,5]triazin-7-ylamine (0.25 mmol; see Example 13(a) above) was dissolved in 4 mL of CH₂Cl₂ along with 1.2 eq of 4-fluorobenzaldehyde and 2 eq of sodium triacetoxyborohydride. The reaction mixture was stirred at room temperature for 18 hours. It was then concentrated and purified by preparative HPLC to afford the title compound. $^1$H NMR (400 Hz, DMSO-d₆) δ 8.20 (brs, 1H), 7.80 (d, J=1.0 Hz, 1H), 7.00 (d, J=3.6 Hz, 1H), 7.2-7.4 (m, 4H), 6.60 (dd, J=3.6, 1.0 Hz, 1H), 6.30 (s, 1H), 4.80 (brs, 2H), 4.20-4.30 (m, 8H). MS m/z: 407 [M+H]⁺.

EXAMPLE 15

5-[5-(4-Chloro-benzyl)-hexahydro-pyrrolo[3,4-b]pyrrol-1-yl]-2-furan-2-yl-[1,2,4]triazolo[1,5-a][1,3,5]triazin-7-ylamine Tert-butyl 2,7-diazabicyclo[3.3.0]octane-7-carboxylate (0.5 mmol; see U.S. Pat. No. 5,071,999) was added to a mixture of 2-furan-2-yl-5-methanesulfonyl-[1,2,4]triazolo[1,5-a][1,3,5]triazin-7-ylamine (0.5 mmol, 1 eq.; see *J. Chem. Soc. Perkin Trans.* 1, 801 (1995)) and Et₃N (0.6 mmol) in 5 mL of CH₃CN. The reaction mixture was stirred at reflux for 2 hours. It was then cooled to room temperature and concentrated. The resulting residue was taken up in EtOAc, washed with brine, dried with Na₂SO₄, and concentrated under reduced pressure. This material (1-(7-amino-2-furan-2-yl-[1,2,4]triazolo[1,5-a][1,3,5]triazin-5-yl)-hexahydro-pyrrolo[3,4-b]pyrrole-5-carboxylic acid tert-butyl ester) was dissolved in 2 mL of 25% TFA in CH₂Cl₂ and allowed to stand at room temperature for 2 hours. It was then concentrated and the resulting residue was dissolved in 3 mL of CH₃CN along with 0.5 mmol of 4-chlorobenzyl chloride and 0.8 mmol of Et₃N. The resulting reaction mixture was stirred at room temperature for 18 hours. It was then concentrated and purified by preparative HPLC to afford the title compound. $^1$H NMR (400 Hz, DMSO-d₆) δ 8.20 (brs, 1H), 7.70

(d, J=1.0 Hz, 1H), 7.10 (d, J=3.6 Hz, 1H), 7.0-7.30 (m, 4H) 6.60 (dd, J=3.6, 1.0 Hz, 1H), 4.80 (brs, 2H), 2.30-3.8 (m, 10H). MS m/z: 438 [M+H]+.

EXAMPLE 16

5-[1-(2,6-Dichloro-benzyl)-hexahydro-pyrrolo[3,4-b]pyrrol-5-yl]-2-furan-2-yl-[1,2,4]triazolo[1,5-a][1,3,5]triazin-7-ylamine Tert-butyl 2,7-diazabicyclo[3.3.0]octane-7-carboxylate (0.3 mmol; see U.S. Pat. No. 5,071,999) dissolved in 2 mL of $CH_3CN$ along with 0.3 mmol of 2,6-dichlorobenzyl chloride and 0.5 mmol of $Et_3N$. The reaction mixture was stirred at room temperature for 18 hours. It was then diluted with EtOAc, washed with brine, dried with $Na_2SO_4$, and concentrated under reduced pressure. The resulting residue was dissolved in 2 mL of 25% TFA in $CH_2Cl_2$ and allowed to stand at room temperature for 3 hours. It was then concentrated to dryness. The resulting residue was dissolved in 3 mL of $CH_3CN$ along with 0.3 mmol of 2-furan-2-yl-5-methanesulfonyl-[1,2,4]triazolo[1,5-a][1,3,5]triazin-7-ylamine (see *J. Chem. Soc. Perkin Trans.* 1, 801 (1995)) and 0.8 mmol of $Et_3N$. The reaction mixture was stirred at reflux for 3 hours. It was then concentrated and purified by preparative HPLC to afford the title compound. $^1$H NMR (400 Hz, DMSO-$d_6$) δ 8.20 (brs, 1H), 7.8 (d, J=1.0 Hz, 1H), 7.30 (d, J=3.6 Hz, 1H), 7.1-7.30 (m, 3H) 6.60 (dd, J=3.6, 1.0 Hz, 1H), 4.80 (brs, 2H), 2.30-3.8 (m, 10H). MS m/z: 472 [M+H]+.

EXAMPLE 17

7-(1-Benzyl-hexahydro-pyrrolo[3,4-b]pyrrol-5-yl)-2-furan-2-yl-[1,2,4]triazolo[1,5-c]pyrimidin-5-ylamine 2-Benzyl-2,7-diazabicyclo[3.3.0]octane (1.2 mmol; see U.S. Pat. No. 5,071,999) was dissolved in 2 mL of DMSO along with 7-chloro-2-furan-2-yl-[1,2,4]triazolo[1,5-c]pyrimidin-5-ylamine (0.25 mmol; see U.S. Pat. No. 6,222,035 B1) and CsF (0.3 mmol). The reaction mixture was stirred at 120° C. for 18 hours. It was then cooled to room temperature and purified by preparative HPLC to afford the title compound. $^1$H NMR (400 Hz, DMSO-$d_6$) 7.60 (d, J=1.0 Hz, 1H), 7.28 (br s, 2H), 7.22 (d, J=3.6 Hz, 1H), 7.0-7.2 (m, 5H), 6.68 (dd, J=3.6 Hz, 1.0 Hz, 1H) 5.4 (s, 1H), 3.8 (br s, 2H), 2.2-3.2 (m, 10H). MS: m/z: 402 [M+H]+.

EXAMPLE 18

7-[5-(2,6-Difluoro-benzyl)-2,5-diaza-bicyclo[2.2.1]hept-2-yl]-2-furan-2-yl-[1,2,4]triazolo[1,5-c]pyrimidin-5-ylamine 7-Chloro-2-furan-2-yl-[1,2,4]triazolo[1,5-c]pyrimidin-5-ylamine (0.5 mmol; see U.S. Pat. No. 6,222,035 B1) was dissolved in 4 mL of DMSO along 2 mmol of 2,5-diaza-bicyclo[2.2.1]heptane-2-carboxylic acid tert-butyl ester (Aldrich-Sigma, St. Louis, Mo.) and 0.6 mmol of CsF. The reaction mixture was stirred at 120° C. for 18 hours. It was then diluted with EtOAc, washed with water and brine, dried with $Na_2SO_4$, and concentrated. The resulting residue was dissolved in 4 mL of 25% TFA in $CH_2Cl_2$ and allowed to stand at room temperature for 18 hours. It was then concentrated to afford the TFA salt of 7-(2,5-diaza-bicyclo[2.2.1]hept-2-yl)-2-furan-2-yl-[1,2,4]triazolo[1,5-c]pyrimidin-5-ylamine. This material was dissolved in 3 mL of $CH_2Cl_2$ along with 0.6 mmol of 2,6-difluorobenzaldehyde and 1 mmol of sodium triacetoxyborohydride. The resulting reaction mixture was concentrated and purified by preparative HPLC to afford the title compound. $^1$H NMR (400 Hz, DMSO-$d_6$) δ 7.80 (d, J=1.0 Hz, 1H), 7.00 (d, J=3.6 Hz, 1H), 7.2-7.4 (m, 3H), 6.60 (dd, J=3.6, 1.0 Hz, 1H), 5.7 (s, 1H), 4.80 (brs, 2H), 2.4-3.6 (m, 8H). MS m/z: 424 [M+H]+.

EXAMPLE 19

7-[5-(3,5-Dimethyl-isoxazol-4-ylmethyl)-2,5-diaza-bicyclo[2.2.1]hept-2-yl]-2-furan-2-yl-[1,2,4]triazolo[1,5-c]pyrimidin-5-ylamine The TFA salt of 7-(2,5-diaza-bicyclo[2.2.1]hept-2-yl)-2-furan-2-yl-[1,2,4]triazolo[1,5-c]pyrimidin-5-ylamine (0.3 mmol; see Example 18 above) was dissolved in 3 mL of $CH_3CN$ along with 0.3 mmol of 4-chloromethyl-3,5-dimethyl-isoxazole (Aldrich-Sigma, St. Louis, Mo.) and 0.5 mmol of $Et_3N$. The reaction mixture was stirred at room temperature for 18 hours. It was then concentrated and purified by preparative HPLC to afford the title compound. $^1$H NMR (400 Hz, DMSO-$d_6$) δ 7.80 (d, J=1.0 Hz, 1H), 7.00 (d, J=3.6 Hz, 1H), 6.60 (dd, J=3.6, 1.0 Hz, 1H), 5.7 (s, 1H), 4.80 (brs, 2H), 2.4-3.6 (m, 14H). MS m/z: 407 [M+H]+.

EXAMPLE 20

5-(1-Benzyl-hexahydro-pyrrolo[3,4-b]pyrrol-5-yl)-2-furan-2-yl-[1,2,4]triazolo[1,5-a]pyrimidin-7-ylamine 5-Chloro-2-furan-2-yl-[1,2,4]triazolo[1,5-a]pyrimidin-7-ylamine (0.5 mmol; see WO 99/43678 A1) was dissolved in 4 mL of DMSO along with 2-benzyl-2,7-diazabicyclo[3.3.0]octane (2 mmol; see U.S. Pat. No. 5,071,999) and 0.7 mmol of CsF. The reaction mixture was stirred at 120° C. for 8 hours. It was then cooled to room temperature and purified by preparative HPLC to afford the title compound. $^1$H NMR (400 Hz, DMSO-$d_6$) 7.60 (d, J=1.0 Hz, 1H), 7.28 (br s, 2H), 7.22 (d, J=3.6 Hz, 1H), 7.0-7.2 (m, 5H), 6.68 (dd, J=3.6 Hz, 1.0 Hz, 1H) 5.2 (s, 1H), 3.8 (br s, 2H), 2.2-3.2 (m, 10H). m/z: 402 [M+H]+.

The compounds listed in the following table were prepared in an analogous manner as described in the methods and examples above. The mass spectroscopy data of these compounds are included in the table.

| Example | Compound Name | Mass Spec. (m/z) | Synthetic Method |
|---|---|---|---|
| Ex. 21 | (±)-2-Furan-2-yl-5-(octahydro-pyrido[1,2-a]pyrazin-2-yl)-[1,2,4]triazolo[1,5-a][1,3,5]triazin-7-ylamine | 341 [M + H]+ | Ex. 1 |
| Ex. 22 | (±)-2-Furan-2-yl-7-(octahydro-pyrido[1,2-a]pyrazin-2-yl)-[1,2,4]triazolo[1,5-c]pyrimidin-5-ylamine | 340 [M + H]+ | Ex. 3 |

| Example | Compound Name | Mass Spec. (m/z) | Synthetic Method |
|---|---|---|---|
| Ex. 23 | (±)-2-Furan-2-yl-5-(octahydro-pyrido[1,2-a]pyrazin-2-yl)-[1,2,4]triazolo[1,5-a]pyrimidin-7-ylamine | 340 [M + H]+ | Ex. 4 |
| Ex. 24 | (±)-2-Furan-2-yl-5-(hexahydro-pyrrolo[1,2-a]pyrazin-2-yl)-[1,2,4]triazolo[1,5-a][1,3,5]triazin-7-ylamine | 327 [M + H]+ | Ex. 1 |
| Ex. 25 | (S)-2-Furan-2-yl-5-(hexahydro-pyrrolo[1,2-a]pyrazin-2-yl)-[1,2,4]triazolo[1,5-a][1,3,5]triazin-7-ylamine | 327 [M + H]+ | Ex. 1 |
| Ex. 26 | (S)-2-Furan-2-yl-7-(hexahydro-pyrrolo[1,2-a]pyrazin-2-yl)-[1,2,4]triazolo[1,5-c]pyrimidin-5-ylamine | 326 [M + H]+ | Ex. 3 |
| Ex. 27 | (S)-2-Furan-2-yl-5-(hexahydro-pyrrolo[1,2-a]pyrazin-2-yl)-[1,2,4]triazolo[1,5-a]pyrimidin-7-ylamine | 326 [M + H]+ | Ex. 4 |
| Ex. 28 | (3S,8aS)-5-(3-Benzyl-hexahydro-pyrrolo[1,2-a]pyrazin-2-yl)-2-furan-2-yl-[1,2,4]triazolo[1,5-a][1,3,5]triazin-7-ylamine | 417 [M + H]+ | Ex. 1 |
| Ex. 29 | (7RS,9aSR)-[2-(7-Amino-2-furan-2-yl-[1,2,4]triazolo[1,5-a][1,3,5]triazin-5-yl)-octahydro-pyrido[1,2-a]pyrazin-7-yl]-methanol | 371 [M + H]+ | Ex. 1 |
| Ex. 30 | (7RS,9aSR)-[[2-(5-Amino-2-furan-2-yl-[1,2,4]triazolo[1,5-c]pyrimidin-7-yl)-octahydro-pyrido[1,2-a]pyrazin-7-yl]-methanol | 370 [M + H]+ | Ex. 3 |
| Ex. 31 | (7RS,9aSR)-[2-(7-Amino-2-furan-2-yl-[1,2,4]triazolo[1,5-a]pyrimidin-5-yl)-octahydro-pyrido[1,2-a]pyrazin-7-yl]-methanol | 370 [M + H]+ | Ex. 4 |
| Ex. 32 | (6RS,9aRS)-[2-(5-Amino-2-furan-2-yl-[1,2,4]triazolo[1,5-c]pyrimidin-7-yl)-octahydro-pyrido[1,2-a]pyrazin-6-yl]-methanol | 370 [M + H]+ | Ex. 3 |
| Ex. 33 | (6RS,9aRS)-[2-(7-Amino-2-furan-2-yl-[1,2,4]triazolo[1,5-a]pyrimidin-5-yl)-octahydro-pyrido[1,2-a]pyrazin-6-yl]-methanol | 370 [M + H]+ | Ex. 4 |
| Ex. 34 | (7RS,9aRS)-7-[7-(2,4-Difluoro-phenoxymethyl)-octahydro-pyrido[1,2-a]pyrazin-2-yl]-2-furan-2-yl-[1,2,4]triazolo[1,5-c]pyrimidin-5-ylamine | 482 [M + H]+ | Ex. 5 |
| Ex. 35 | (7RS,9aRS)-2-Furan-2-yl-7-(7-phenoxymethyl-octahydro-pyrido[1,2-a]pyrazin-2-yl)-[1,2,4]triazolo[1,5-c]pyrimidin-5-ylamine | 446 [M + H]+ | Ex. 5 |
| Ex. 36 | (7RS,9aRS)-7-[7-(2-Fluoro-phenoxymethyl)-octahydro-pyrido[1,2-a]pyrazin-2-yl]-2-furan-2-yl-[1,2,4]triazolo[1,5-c]pyrimidin-5-ylamine | 464 [M + H]+ | Ex. 5 |
| Ex. 37 | (7RS,9aRS)-7-[7-(3-Fluoro-phenoxymethyl)-octahydro-pyrido[1,2-a]pyrazin-2-yl]-2-furan-2-yl-[1,2,4]triazolo[1,5-c]pyrimidin-5-ylamine | 464 [M + H]+ | Ex. 5 |
| Ex. 38 | (7RS,9aRS)-5-[7-(2,4-Difluoro-phenoxymethyl)-octahydro-pyrido[1,2-a]pyrazin-2-yl]-2-furan-2-yl-[1,2,4]triazolo[1,5-a]pyrimidin-7-ylamine | 482 [M + H]+ | Ex. 5 |
| Ex. 39 | (7RS,9aRS)-2-Furan-2-yl-5-[7-(quinolin-6-yloxymethyl)-octahydro-pyrido[1,2-a]pyrazin-2-yl]-[1,2,4]triazolo[1,5-a]pyrimidin-7-ylamine | 497 [M + H]+ | Ex. 5 |
| Ex. 40 | (7RS,9aRS)-2-Furan-2-yl-5-(7-phenoxymethyl-octahydro-pyrido[1,2-a]pyrazin-2-yl)-[1,2,4]triazolo[1,5-a]pyrimidin-7-ylamine | 446 [M + H]+ | Ex. 5 |
| Ex. 41 | (7RS,9aRS)-2-Furan-2-yl-5-[7-(pyridin-2-yloxymethyl)-octahydro-pyrido[1,2-a]pyrazin-2-yl]-[1,2,4]triazolo[1,5-a]pyrimidin-7-ylamine | 447 [M + H]+ | Ex. 5 |
| Ex. 42 | (7RS,9aRS)-2-Furan-2-yl-5-[7-(pyridin-3-yloxymethyl)-octahydro-pyrido[1,2-a]pyrazin-2-yl]-[1,2,4]triazolo[1,5-a]pyrimidin-7-ylamine | 447 [M + H]+ | Ex. 5 |
| Ex. 43 | (7RS,9aRS)-2-Furan-2-yl-5-[7-(pyridin-4-yloxymethyl)-octahydro-pyrido[1,2-a]pyrazin-2-yl]-[1,2,4]triazolo[1,5-a]pyrimidin-7-ylamine | 447 [M + H]+ | Ex. 5 |
| Ex. 44 | (7RS,9aRS)-5-[7-(Benzo[1,3]dioxol-5-yloxymethyl)-octahydro-pyrido[1,2-a]pyrazin-2-yl]-2-furan-2-yl-[1,2,4]triazolo[1,5-a]pyrimidin-7-ylamine | 490 [M + H]+ | Ex. 5 |
| Ex. 45 | (7RS,9aRS)-2-Furan-2-yl-5-[7-(1H-indol-5-yloxymethyl)-octahydro-pyrido[1,2-a]pyrazin-2-yl]-[1,2,4]triazolo[1,5-a]pyrimidin-7-ylamine | 485 [M + H]+ | Ex. 5 |
| Ex. 46 | (7RS,9aRS)-5-[7-(3-Amino-phenoxymethyl)-octahydro-pyrido[1,2-a]pyrazin-2-yl]-2-furan-2-yl-[1,2,4]triazolo[1,5-a]pyrimidin-7-ylamine | 461 [M + H]+ | Ex. 5 |
| Ex. 47 | (7RS,9aRS)-5-[7-(2,4-Difluoro-phenoxymethyl)-octahydro-pyrido[1,2-a]pyrazin-2-yl]-2-furan-2-yl-[1,2,4]triazolo[1,5-a][1,3,5]triazin-7-ylamine | 483 [M + H]+ | Ex. 5 |
| Ex. 48 | (7RS,9aRS)-2-Furan-2-yl-5-[7-(quinolin-6-yloxymethyl)-octahydro-pyrido[1,2-a]pyrazin-2-yl]-[1,2,4]triazolo[1,5-a][1,3,5]triazin-7-ylamine | 498 [M + H]+ | Ex. 5 |
| Ex. 49 | (7RS,9aRS)-2-Furan-2-yl-5-(7-phenoxymethyl-octahydro-pyrido[1,2-a]pyrazin-2-yl)-[1,2,4]triazolo[1,5-a][1,3,5]triazin-7-ylamine | 447 [M + H]+ | Ex. 5 |

-continued

| Example | Compound Name | Mass Spec. (m/z) | Synthetic Method |
|---|---|---|---|
| Ex. 50 | (7RS,9aRS)-2-Furan-2-yl-5-[7-(5,6,7,8-tetrahydro-naphthalen-2-yloxymethyl)-octahydro-pyrido[1,2-a]pyrazin-2-yl]-[1,2,4]triazolo[1,5-a][1,3,5]triazin-7-ylamine | 501 [M + H]+ | Ex. 5 |
| Ex. 51 | (7RS,9aRS)-5-[7-(2-Fluoro-phenoxymethyl)-octahydro-pyrido[1,2-a]pyrazin-2-yl]-2-furan-2-yl-[1,2,4]triazolo[1,5-a][1,3,5]triazin-7-ylamine | 465 [M + H]+ | Ex. 5 |
| Ex. 52 | (7RS,9aRS)-5-[7-(3-Fluoro-phenoxymethyl)-octahydro-pyrido[1,2-a]pyrazin-2-yl]-2-furan-2-yl-[1,2,4]triazolo[1,5-a][1,3,5]triazin-7-ylamine | 465 [M + H]+ | Ex. 5 |
| Ex. 53 | (7RS,9aRS)-5-[7-(4-Fluoro-phenoxymethyl)-octahydro-pyrido[1,2-a]pyrazin-2-yl]-2-furan-2-yl-[1,2,4]triazolo[1,5-a][1,3,5]triazin-7-ylamine | 465 [M + H]+ | Ex. 5 |
| Ex. 54 | (7RS,9aRS)-2-Furan-2-yl-5-[7-(4-methoxy-phenoxymethyl)-octahydro-pyrido[1,2-a]pyrazin-2-yl]-[1,2,4]triazolo[1,5-a][1,3,5]triazin-7-ylamine | 477 [M + H]+ | Ex. 5 |
| Ex. 55 | (7RS,9aRS)-2-Furan-2-yl-5-[7-(2,3,5-trifluoro-phenoxymethyl)-octahydro-pyrido[1,2-a]pyrazin-2-yl]-[1,2,4]triazolo[1,5-a][1,3,5]triazin-7-ylamine | 501 [M + H]+ | Ex. 5 |
| Ex. 56 | (7RS,9aRS)-2-Furan-2-yl-5-[7-(2,4,6-trifluoro-phenoxymethyl)-octahydro-pyrido[1,2-a]pyrazin-2-yl]-[1,2,4]triazolo[1,5-a][1,3,5]triazin-7-ylamine | 501 [M + H]+ | Ex. 5 |
| Ex. 57 | (7RS,9aRS)-2-Furan-2-yl-5-[7-(pyridin-2-yloxymethyl)-octahydro-pyrido[1,2-a]pyrazin-2-yl]-[1,2,4]triazolo[1,5-a][1,3,5]triazin-7-ylamine | 448 [M + H]+ | Ex. 5 |
| Ex. 58 | (7RS,9aRS)-2-Furan-2-yl-5-[7-(pyridin-3-yloxymethyl)-octahydro-pyrido[1,2-a]pyrazin-2-yl]-[1,2,4]triazolo[1,5-a][1,3,5]triazin-7-ylamine | 498 [M + H]+ | Ex. 5 |
| Ex. 59 | (7RS,9aRS)-2-Furan-2-yl-5-[7-(pyridin-4-yloxymethyl)-octahydro-pyrido[1,2-a]pyrazin-2-yl]-[1,2,4]triazolo[1,5-a][1,3,5]triazin-7-ylamine | 448 [M + H]+ | Ex. 5 |
| Ex. 60 | (7RS,9aRS)-2-Furan-2-yl-5-[7-(4-trifluoromethyl-pyrimidin-2-yloxymethyl)-octahydro-pyrido[1,2-a]pyrazin-2-yl]-[1,2,4]triazolo[1,5-a][1,3,5]triazin-7-ylamine | 517 [M + H]+ | Ex. 5 |
| Ex. 61 | (7RS,9aRS)-2-Furan-2-yl-5-[7-(6-trifluoromethyl-pyrimidin-4-yloxymethyl)-octahydro-pyrido[1,2-a]pyrazin-2-yl]-[1,2,4]triazolo[1,5-a][1,3,5]triazin-7-ylamine | 517 [M + H]+ | Ex. 5 |
| Ex. 62 | (7RS,9aRS)-2-Furan-2-yl-5-[7-(quinazolin-2-yloxymethyl)-octahydro-pyrido[1,2-a]pyrazin-2-yl]-[1,2,4]triazolo[1,5-a][1,3,5]triazin-7-ylamine | 499 [M + H]+ | Ex. 5 |
| Ex. 63 | (7RS,9aRS)-2-Furan-2-yl-5-[7-(isoquinolin-3-yloxymethyl)-octahydro-pyrido[1,2-a]pyrazin-2-yl]-[1,2,4]triazolo[1,5-a][1,3,5]triazin-7-ylamine | 498 [M + H]+ | Ex. 5 |
| Ex. 64 | (7RS,9aRS)-2-Furan-2-yl-5-[7-(isoquinolin-5-yloxymethyl)-octahydro-pyrido[1,2-a]pyrazin-2-yl]-[1,2,4]triazolo[1,5-a][1,3,5]triazin-7-ylamine | 498 [M + H]+ | Ex. 5 |
| Ex. 65 | (7RS,9aRS)-2-Furan-2-yl-5-[7-(1H-pyrazolo[3,4-d]pyrimidin-4-yloxymethyl)-octahydro-pyrido[1,2-a]pyrazin-2-yl]-[1,2,4]triazolo[1,5-a][1,3,5]triazin-7-ylamine | 489 [M + H]+ | Ex. 5 |
| Ex. 66 | (7RS,9aRS)-2-Furan-2-yl-5-(7-imidazol-1-ylmethyl-octahydro-pyrido[1,2-a]pyrazin-2-yl)-[1,2,4]triazolo[1,5-a][1,3,5]triazin-7-ylamine | 421 [M + H]+ | Ex. 5 |
| Ex. 67 | (7RS,9aRS)-2-Furan-2-yl-5-(7-[1,2,4]triazol-1-ylmethyl-octahydro-pyrido[1,2-a]pyrazin-2-yl)-[1,2,4]triazolo[1,5-a][1,3,5]triazin-7-ylamine | 422 [M + H]+ | Ex. 5 |
| Ex. 68 | (7RS,9aRS)-2-Furan-2-yl-5-(7-tetrazol-1-ylmethyl-octahydro-pyrido[1,2-a]pyrazin-2-yl)-[1,2,4]triazolo[1,5-a][1,3,5]triazin-7-ylamine | 423 [M + H]+ | Ex. 5 |
| Ex. 69 | (7RS,9aSR)-2-Furan-2-yl-7-[7-(4-methoxy-phenoxymethyl)-octahydro-pyrido[1,2-a]pyrazin-2-yl]-[1,2,4]triazolo[1,5-c]pyrimidin-5-ylamine | 476 [M + H]+ | Ex. 5 |
| Ex. 70 | (7RS,9aSR)-2-Furan-2-yl-7-(7-phenoxymethyl-octahydro-pyrido[1,2-a]pyrazin-2-yl)-[1,2,4]triazolo[1,5-c]pyrimidin-5-ylamine | 446 [M + H]+ | Ex. 5 |
| Ex. 71 | (7RS,9aSR)-2-Furan-2-yl-7-[7-(5,6,7,8-tetrahydro-naphthalen-2-yloxymethyl)-octahydro-pyrido[1,2-a]pyrazin-2-yl]-[1,2,4]triazolo[1,5-c]pyrimidin-5-ylamine | 500 [M + H]+ | Ex. 5 |
| Ex. 72 | (7RS,9aSR)-5-[7-(2,4-Difluoro-phenoxymethyl)-octahydro-pyrido[1,2-a]pyrazin-2-yl]-2-furan-2-yl-[1,2,4]triazolo[1,5-a][1,3,5]triazin-7-ylamine | 483 [M + H]+ | Ex. 5 |
| Ex. 73 | (7RS,9aSR)-2-Furan-2-yl-5-[7-(4-methoxy-phenoxymethyl)-octahydro-pyrido[1,2-a]pyrazin-2-yl]-[1,2,4]triazolo[1,5-a][1,3,5]triazin-7-ylamine | 477 [M + H]+ | Ex. 5 |
| Ex. 74 | (7RS,9aSR)-2-Furan-2-yl-5-(7-phenoxymethyl-octahydro-pyrido[1,2-a]pyrazin-2-yl)-[1,2,4]triazolo[1,5-a][1,3,5]triazin-7-ylamine | 447 [M + H]+ | Ex. 5 |

-continued

| Example | Compound Name | Mass Spec. (m/z) | Synthetic Method |
|---|---|---|---|
| Ex. 75 | (7RS,9aSR)-2-Furan-2-yl-5-[7-(5,6,7,8-tetrahydro-naphthalen-2-yloxymethyl)-octahydro-pyrido[1,2-a]pyrazin-2-yl]-[1,2,4]triazolo[1,5-a][1,3,5]triazin-7-ylamine | 501 [M + H]+ | Ex. 5 |
| Ex. 76 | (7RS,9aSR)-2-Furan-2-yl-5-[7-(pyridin-2-yloxymethyl)-octahydro-pyrido[1,2-a]pyrazin-2-yl]-[1,2,4]triazolo[1,5-a][1,3,5]triazin-7-ylamine | 448 [M + H]+ | Ex. 5 |
| Ex. 77 | (7RS,9aSR)-2-Furan-2-yl-5-[7-(pyridin-3-yloxymethyl)-octahydro-pyrido[1,2-a]pyrazin-2-yl]-[1,2,4]triazolo[1,5-a][1,3,5]triazin-7-ylamine | 448 [M + H]+ | Ex. 5 |
| Ex. 78 | (7RS,9aSR)-2-Furan-2-yl-5-[7-(pyridin-4-yloxymethyl)-octahydro-pyrido[1,2-a]pyrazin-2-yl]-[1,2,4]triazolo[1,5-a][1,3,5]triazin-7-ylamine | 448 [M + H]+ | Ex. 5 |
| Ex. 79 | (7RS,9aSR)-5[7-(Benzo[1,3]dioxol-5-yloxymethyl)-octahydro-pyrido[1,2-a]pyrazin-2-yl]-2-furan-2-yl-[1,2,4]triazolo[1,5-a][1,3,5]triazin-7-ylamine | 491 [M + H]+ | Ex. 5 |
| Ex. 80 | (7RS,9aSR)-2-Furan-2-yl-5-[7-(quinazolin-2-yloxymethyl)-octahydro-pyrido[1,2-a]pyrazin-2-yl]-[1,2,4]triazolo[1,5-a][1,3,5]triazin-7-ylamine | 499 [M + H]+ | Ex. 5 |
| Ex. 81 | (7RS,9aSR)-2-Furan-2-yl-5-[7-(quinolin-2-yloxymethyl)-octahydro-pyrido[1,2-a]pyrazin-2-yl]-[1,2,4]triazolo[1,5-a][1,3,5]triazin-7-ylamine | 498 [M + H]+ | Ex. 5 |
| Ex. 82 | (7RS,9aSR)-2-Furan-2-yl-5-[7-(isoquinolin-3-yloxymethyl)-octahydro-pyrido[1,2-a]pyrazin-2-yl]-[1,2,4]triazolo[1,5-a][1,3,5]triazin-7-ylamine | 498 [M + H]+ | Ex. 5 |
| Ex. 83 | (7RS,9aSR)-2-Furan-2-yl-5-[7-(isoquinolin-5-yloxymethyl)-octahydro-pyrido[1,2-a]pyrazin-2-yl]-[1,2,4]triazolo[1,5-a][1,3,5]triazin-7-ylamine | 498 [M + H]+ | Ex. 5 |
| Ex. 84 | (7RS,9aSR)-5-[7-(2-Fluoro-phenoxymethyl)-octahydro-pyrido[1,2-a]pyrazin-2-yl]-2-furan-2-yl-[1,2,4]triazolo[1,5-a][1,3,5]triazin-7-ylamine | 465 [M + H]+ | Ex. 5 |
| Ex. 85 | (7RS,9aSR)-5-[7-(4-Fluoro-phenoxymethyl)-octahydro-pyrido[1,2-a]pyrazin-2-yl]-2-furan-2-yl-[1,2,4]triazolo[1,5-a][1,3,5]triazin-7-ylamine | 465 [M + H]+ | Ex. 5 |
| Ex. 86 | (6RS,9aRS)-[2-Furan-2-yl-5-[6-(quinolin-5-yloxymethyl)-octahydro-pyrido[1,2-a]pyrazin-2-yl]-[1,2,4]triazolo[1,5-a]pyrimidin-7-ylamine | 497 [M + H]+ | Ex. 5 |
| Ex. 87 | (6RS,9aRS)-[5-[6-(3-Amino-phenoxymethyl)-octahydro-pyrido[1,2-a]pyrazin-2-yl]-2-furan-2-yl-[1,2,4]triazolo[1,5-a]pyrimidin-7-ylamine | 461 [M + H]+ | Ex. 5 |
| Ex. 88 | (6RS,9aRS)-[5-[6-(Benzo[1,3]dioxol-5-yloxymethyl)-octahydro-pyrido[1,2-a]pyrazin-2-yl]-2-furan-2-yl-[1,2,4]triazolo[1,5-a]pyrimidin-7-ylamine | 490 [M + H]+ | Ex. 5 |
| Ex. 89 | (6RS,9aRS)-[2-Furan-2-yl-5-[6-(pyridin-3-yloxymethyl)-octahydro-pyrido[1,2-a]pyrazin-2-yl]-[1,2,4]triazolo[1,5-a]pyrimidin-7-ylamine | 447 [M + H]+ | Ex. 5 |
| Ex. 90 | (6RS,9aRS)-[2-Furan-2-yl-5-(6-phenoxymethyl-octahydro-pyrido[1,2-a]pyrazin-2-yl)-[1,2,4]triazolo[1,5-a][1,3,5]triazin-7-ylamine | 447 [M + H]+ | Ex. 5 |
| Ex. 91 | (6RS,9aRS)-[2-Furan-2-yl-5-[6-(5,6,7,8-tetrahydro-naphthalen-1-yloxymethyl)-octahydro-pyrido[1,2-a]pyrazin-2-yl]-[1,2,4]triazolo[1,5-a][1,3,5]triazin-7-ylamine | 501 [M + H]+ | Ex. 5 |
| Ex. 92 | (6RS,9aRS)-[5-[6-(3-Amino-phenoxymethyl)-octahydro-pyrido[1,2-a]pyrazin-2-yl]-2-furan-2-yl-[1,2,4]triazolo[1,5-a][1,3,5]triazin-7-ylamine | 462 [M + H]+ | Ex. 5 |
| Ex. 93 | (6RS,9aRS)-[5-[6-(Benzo[1,3]dioxol-5-yloxymethyl)-octahydro-pyrido[1,2-a]pyrazin-2-yl]-2-furan-2-yl-[1,2,4]triazolo[1,5-a][1,3,5]triazin-7-ylamine | 491 [M + H]+ | Ex. 5 |
| Ex. 94 | (6RS,9aRS)-[2-Furan-2-yl-5-[6-(1H-indol-s-yloxymethyl)-octahydro-pyrido[1,2-a]pyrazin-2-yl]-[1,2,4]triazolo[1,5-a][1,3,5]triazin-7-ylamine | 486 [M + H]+ | Ex. 5 |
| Ex. 95 | (6RS,9aRS)-[1-[2-(7-Amino-2-furan-2-yl[1,2,4]triazolo[1,5-a][1,3,5]triazin-5-yl)-octahydro-pyrido[1,2-a]pyrazin-6-ylmethyl]-1H-indol-5-ol | 486 [M + H]+ | Ex. 6 |
| Ex. 96 | (7RS,9aRS)-2-Furan-2-yl-N5-(2-pyrimidin-2-yl-octahydro-pyrido[1,2-a]pyrazin-7-ylmethyl)-[1,2,4]triazolo[1,5-a]pyrimidine-5,7-diamine | 447 [M + H]+ | Ex. 6 |
| Ex. 97 | (7RS,9aRS)-3-Amino-5-{7-[(7-amino-2-furan-2-yl-[1,2,4]triazolo[1,5-a][1,3,5]triazin-5-ylamino)-methyl]-octahydro-pyrido[1,2-a]pyrazin-2-yl}-6-chloro-pyrazine-2-carboxylic acid methyl ester | 556 M + 2 | Ex. 6 |
| Ex. 98 | (7RS,9aRS)-N5-[2-(3,5-Difluoro-phenyl)-octahydro-pyrido[1,2-a]pyrazin-7-ylmethyl]-furan-2-yl-[1,2,4]triazolo[1,5-a][1,3,5]triazine-5,7-diamine | 482 [M + H]+ | Ex. 6 |
| Ex. 99 | (7RS,9aRS)-N5-[2-(2,4-Difluoro-benzyl)-octahydro-pyrido[1,2-a]pyrazin-7-ylmethyl]-2-furan-2-yl-[1,2,4]triazolo[1,5-a]pyrimidine-5,7-diamine | 495 [M + H]+ | Ex. 6 |

-continued

| Example | Compound Name | Mass Spec. (m/z) | Synthetic Method |
|---|---|---|---|
| Ex. 100 | (7RS,9aRS)-N5-[2-(2,4-Difluoro-benzyl)-octahydro-pyrido[1,2-a]pyrazin-7-ylmethyl]-2-furan-2-yl-[1,2,4]triazolo[1,5-a][1,3,5]triazine-5,7-diamine | 496 [M + H]+ | Ex. 6 |
| Ex. 101 | (7RS,9aRS)-5-(7-Aminomethyl-octahydro-pyrido[1,2-a]pyrazin-2-yl)-2-furan-2-yl-[1,2,4]triazolo[1,5-a]pyrimidin-7-ylamine | 369 [M + H]+ | Ex. 9 |
| Ex. 102 | (7RS,9aRS)-7-(7-Aminomethyl-octahydro-pyrido[1,2-a]pyrazin-2-yl)-2-furan-2-yl-[1,2,4]triazolo[1,5-c]pyrimidin-5-ylamine | 369 [M + H]+ | Ex. 9 |
| Ex. 103 | (7RS,9aSR)-5-(7-Aminomethyl-octahydro-pyrido[1,2-a]pyrazin-2-yl)-2-furan-2-yl-[1,2,4]triazolo[1,5-a][1,3,5]triazin-7-ylamine | 370 [M + H]+ | Ex. 9 |
| Ex. 104 | (7RS,9aSR)-5-(7-Aminomethyl-octahydro-pyrido[1,2-a]pyrazin-2-yl)-2-furan-2-yl-[1,2,4]triazolo[1,5-a]pyrimidin-7-ylamine | 369 [M + H]+ | Ex. 9 |
| Ex. 105 | (7RS,9aRS)-5-(7-{[Bis-(2-fluoro-benzyl)-amino]-methyl}-octahydro-pyrido[1,2-a]pyrazin-2-yl)-2-furan-2-yl-[1,2,4]triazolo[1,5-a][1,3,5]triazin-7-ylamine | 586 [M + H]+ | Ex. 10 |
| Ex. 106 | (7RS,9aRS)-5-(7-{[Bis-(2,4-difluoro-benzyl)-amino]-methyl}-octahydro-pyrido[1,2-a]pyrazin-2-yl)-2-furan-2-yl-[1,2,4]triazolo[1,5-a][1,3,5]triazin-7-ylamine | 622 [M + H]+ | Ex. 10 |
| Ex. 107 | (7RS,9aRS)-5-{7-[(2,4-Difluoro-benzylamino)-methyl]-octahydro-pyrido[1,2-a]pyrazin-2-yl}-2-furan-2-yl-[1,2,4]triazolo[1,5-a][1,3,5]triazin-7-ylamine | 496 [M + H]+ | Ex. 12 |
| Ex. 108 | (7RS,9aRS)-5-(7-{[Bis-(2,4,6-trifluoro-benzyl)-amino]-methyl}-octahydro-pyrido[1,2-a]pyrazin-2-yl)-2-furan-2-yl-[1,2,4]triazolo[1,5-a][1,3,5]triazin-7-ylamine | 658 [M + H]+ | Ex. 10 |
| Ex. 109 | (7RS,9aRS)-5-(7-{[Bis-(2,3-difluoro-benzyl)-amino]-methyl}-octahydro-pyrido[1,2-a]pyrazin-2-yl)-2-furan-2-yl-[1,2,4]triazolo[1,5-a][1,3,5]triazin-7-ylamine | 622 [M + H]+ | Ex. 10 |
| Ex. 110 | (7RS,9aRS)-5-(7-{[Bis-(2,6-difluoro-benzyl)-amino]-methyl}-octahydro-pyrido[1,2-a]pyrazin-2-yl)-2-furan-2-yl-[1,2,4]triazolo[1,5-a][1,3,5]triazin-7-ylamine | 622 [M + H]+ | Ex. 10 |
| Ex. 111 | (7RS,9aRS)-5-(7-{[Bis-(3,5-difluoro-benzyl)-amino]-methyl}-octahydro-pyrido[1,2-a]pyrazin-2-yl)-2-furan-2-yl-[1,2,4]triazolo[1,5-a][1,3,5]triazin-7-ylamine | 622 [M + H]+ | Ex. 10 |
| Ex. 112 | (7RS,9aRS)-5-(7-{[Bis-(5-chloro-furan-2-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine | 598 [M + H]+ | Ex. 10 |
| Ex. 113 | (7RS,9aRS)-5-{7-[(Bis-pyridin-2-ylmethyl-amino)-methyl]-octahydro-pyrido[1,2-a]pyrazin-2-yl}-2-furan-2-yl-[1,2,4]triazolo[1,5-a][1,3,5]triazin-7-ylamine | 552 [M + H]+ | Ex. 10 |
| Ex. 114 | (7RS,9aRS)-5-{7-[(Bis-pyridin-3-ylmethyl-amino)-methyl]-octahydro-pyrido[1,2-a]pyrazin-2-yl}-2-furan-2-yl-[1,2,4]triazolo[1,5-a][1,3,5]triazin-7-ylamine | 552 [M + H]+ | Ex. 10 |
| Ex. 115 | (7RS,9aRS)-2-Furan-2-yl-5-(7-{[(pyridin-3-ylmethyl)-amino]-methyl}-octahydro-pyrido[1,2-a]pyrazin-2-yl)-[1,2,4]triazolo[1,5-a][1,3,5]triazin-7-ylamine | 461 [M + H]+ | Ex. 12 |
| Ex. 116 | (7RS,9aRS)-5-(7-{[Bis-(2-chloro-1-methyl-4-trifluoromethyl-1H-pyrrol-3-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine | 762 [M + H]+ | Ex. 10 |
| Ex. 117 | (7RS,9aRS)-5-(7-{[Bis-(3,5-dimethyl-isoxazol-4-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine | 588 [M + H]+ | Ex. 10 |
| Ex. 118 | (7RS,9aRS)-5-(7-{[(3,5-Dimethyl-isoxazol-4-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine | 479 [M + H]+ | Ex. 12 |
| Ex. 119 | (7RS,9aRS)-5-{7-[(Bis-cyclohexylmethyl-amino)-methyl]-octahydro-pyrido[1,2-a]pyrazin-2-yl}-2-furan-2-yl-[1,2,4]triazolo[1,5-a][1,3,5]triazin-7-ylamine | 562 [M + H]+ | Ex. 10 |
| Ex. 120 | (7RS,9aRS)-5-{7-[(Bis-furan-2-ylmethyl-amino)-methyl]-octahydro-pyrido[1,2-a]pyrazin-2-yl}-2-furan-2-yl-[1,2,4]triazolo[1,5-a][1,3,5]triazin-7-ylamine | 530 [M + H]+ | Ex. 10 |
| Ex. 121 | (7RS,9aRS)-5-(7-{[Bis-(1H-pyrrol-2-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine | 528 [M + H]+ | Ex. 10 |
| Ex. 122 | (7RS,9aRS)-5-(7-{[Bis-(5-chloro-1,3-dimethyl-1H-pyrazol-4-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine | 654 [M + H]+ | Ex. 10 |
| Ex. 123 | (7RS,9aRS)-5-(7-{[(5-Chloro-1,3-dimethyl-1H-pyrazol-4-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine | 512 [M + H]+ | Ex. 12 |

| Example | Compound Name | Mass Spec. (m/z) | Synthetic Method |
|---|---|---|---|
| Ex. 124 | (7RS,9aRS)-5-{7-[(Bis-thiazol-2-ylmethyl-amino)-methyl]-octahydro-pyrido[1,2-a]pyrazin-2-yl}-2-furan-2-yl-[1,2,4]triazolo[1,5-a][1,3,5]triazin-7-ylamine | 564 [M + H]+ | Ex. 10 |
| Ex. 125 | (7RS,9aRS)-5-{7-[(Bis-thiophen-2-ylmethyl-amino)-methyl]-octahydro-pyrido[1,2-a]pyrazin-2-yl}-2-furan-2-yl-[1,2,4]triazolo[1,5-a][1,3,5]triazin-7-ylamine | 562 [M + H]+ | Ex. 10 |
| Ex. 126 | (7RS,9aRS)-5-(7-{[Bis-(5-methyl-thiophen-2-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine | 590 [M + H]+ | Ex. 10 |
| Ex. 127 | (7RS,9aRS)-2-Furan-2-yl-7-[7-(pyrimidin-2-ylaminomethyl)-octahydra-pyrido[1,2-a]pyrazin-2-yl]-[1,2,4]triazolo[1,5-c]pyrimidin-5-ylamine | 447 [M + H]+ | Ex. 11 |
| Ex. 128 | (7RS,9aRS)-7-{7-[(Bis-pyridin-4-ylmethyl-amino)-methyl]-octahydro-pyrido[1,2-a]pyrazin-2-yl}-2-furan-2-yl-[1,2,4]triazolo[1,5-c]pyrimidin-5-ylamine | 551 [M + H]+ | Ex. 10 |
| Ex. 129 | (7RS,9aRS)-7-{7-[(Bis-furan-2-ylmethyl-amino)-methyl]-octahydro-pyrido[1,2-a]pyrazin-2-yl}-2-furan-2-yl-[1,2,4]triazolo[1,5-c]pyrimidin-5-ylamine | 529 [M + H]+ | Ex. 10 |
| Ex. 130 | (7RS,9aRS)-7-(7-{[Bis-(3,5-dimethyl-isoxazol-4-ylmethyl)-amino]-methyl}-octahydro-pyrido[1,2-a]pyrazin-2-yl)-2-furan-2-yl-[1,2,4]triazolo[1,5-c]pyrimidin-5-ylamine | 587 [M + H]+ | Ex. 10 |
| Ex. 131 | (7RS,9aRS)-2-Furan-2-yl-5-[7-(pyrimidin-2-ylaminomethyl)-octahydro-pyrido[1,2-a]pyrazin-2-yl]-[1,2,4]triazolo[1,5-a]pyrimidin-7-ylamine | 447 [M + H]+ | Ex. 11 |
| Ex. 132 | (7RS,9aRS)-5-{7-[(Bis-pyridin-4-ylmethyl-amino)-methyl]-octahydro-pyrido[1,2-a]pyrazin-2-yl}-2-furan-2-yl-[1,2,4]triazolo[1,5-a]pyrimidin-7-ylamine | 551 [M + H]+ | Ex. 10 |
| Ex. 133 | (7RS,9aRS)-5-{7-[(Bis-furan-2-ylmethyl-amino)-methyl]-octahydro-pyrido[1,2-a]pyrazin-2-yl}-2-furan-2-yl-[1,2,4]triazolo[1,5-a]pyrimidin-7-ylamine | 529 [M + H]+ | Ex. 10 |
| Ex. 134 | (7RS,9aRS)-5-(7-{[Bis-(3,5-dimethyl-isoxazal-4-ylmethyl)-amino]-methyl}-octahydro-pyrido[1,2-a]pyrazin-2-yl)-2-furan-2-yl-[1,2,4]triazolo[1,5-a]pyrimidin-7-ylamine | 587 [M + H]+ | Ex. 10 |
| Ex. 135 | (7RS,9aSR)-2-Furan-2-yl-5-[7-(pyrimidin-2-ylaminomethyl)-octahydro-pyrido[1,2-a]pyrazin-2-yl]-[1,2,4]triazolo[1,5-a][1,3,5]triazin-7-ylamine | 448 [M + H]+ | Ex. 11 |
| Ex. 136 | (7RS,9aSR)-5-{7-[(Bis-pyridin-4-ylmethyl-amino)-methyl]-octahydro-pyrido[1,2-a]pyrazin-2-yl}-2-furan-2-yl-[1,2,4]triazolo[1,5-a][1,3,5]triazin-7-ylamine | 552 [M + H]+ | Ex. 10 |
| Ex. 137 | (7RS,9aSR)-2-Furan-2-yl-5-(7-{[(pyridin-4-ylmethyl)-amino]-methyl}-octahydro-pyrido[1,2-a]pyrazin-2-yl)-[1,2,4]triazolo[1,5-a][1,3,5]triazin-7-ylamine | 461 [M + H]+ | Ex. 12 |
| Ex. 138 | (7RS,9aSR)-5-{7-[(Bis-pyridin-3-ylmethyl-amino)-methyl]-octahydro-pyrido[1,2-a]pyrazin-2-yl}-2-furan-2-yl-[1,2,4]triazolo[1,5-a][1,3,5]triazin-7-ylamine | 552 [M + H]+ | Ex. 11 |
| Ex. 139 | (7RS,9aSR)-2-Furan-2-yl-5-(7-{[(pyridin-3-ylmethyl)-amino]-methyl}-octahydro-pyrido[1,2-a]pyrazin-2-yl)-[1,2,4]triazolo[1,5-a][1,3,5]triazin-7-ylamine | 461 [M + H]+ | Ex. 12 |
| Ex. 140 | (7RS,9aSR)-5-{7-[(Bis-furan-2-ylmethyl-amino)-methyl]-octahydro-pyrido[1,2-a]pyrazin-2-yl}-2-furan-2-yl-[1,2,4]triazolo[1,5-a][1,3,5]triazin-7-ylamine | 530 [M + H]+ | Ex. 10 |
| Ex. 141 | (7RS,9aSR)-2-Furan-2-yl-5-(7-{[(furan-2-ylmethyl)-amino]-methyl}-octahydro-pyrido[1,2-a]pyrazin-2-yl)-[1,2,4]triazolo[1,5-a][1,3,5]triazin-7-ylamine | 450 [M + H]+ | Ex. 12 |
| Ex. 142 | (7RS,9aSR)-5-(7-{[Bis-(3,5-dimethyl-isoxazol-4-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine | 588 [M + H]+ | Ex. 10 |
| Ex. 143 | (7RS,9aSR)-5-(7-{[(3,5-Dimethyl-isoxazol-4-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine | 479 [M + H]+ | Ex. 12 |
| Ex. 144 | (7RS,9aSR)-2-Furan-2-yl-5-[7-(pyrimidin-2-ylaminomethyl)-octahydro-pyrido[1,2-a]pyrazin-2-yl]-[1,2,4]triazolo[1,5-a]pyrimidin-7-ylamine | 447 [M + H]+ | Ex. 11 |
| Ex. 145 | (7RS,9aSR)-5-{7-[(Bis-furan-2-ylmethyl-amino)-methyl]-octahydro-pyrido[1,2-a]pyrazin-2-yl}-2-furan-2-yl-[1,2,4]triazolo[1,5-a]pyrimidin-7-ylamine | 529 [M + H]+ | Ex. 10 |
| Ex. 146 | (7RS,9aSR)-5-{7-[(Bis-pyridin-4-ylmethyl-amino)-methyl]-octahydro-pyrido[1,2-a]pyrazin-2-yl}-2-furan-2-yl-[1,2,4]triazolo[1,5-a]pyrimidin-7-ylamine | 551 [M + H]+ | Ex. 10 |
| Ex. 147 | (R)-2-Furan-2-yl-5-(hexahydro-pyrrolo[1,2-a]pyrazin-2-yl)-[1,2,4]triazolo[1,5-a][1,3,5]triazin-7-ylamine | 327 [M + H]+ | Ex. 1 |
| Ex. 148 | (R)-2-Furan-2-yl-7-(hexahydro-pyrrolo[1,2-a]pyrazin-2-yl)-[1,2,4]triazolo[1,5-c]pyrimidin-5-ylamine | 327 [M + H]+ | Ex. 3 |
| Ex. 149 | 2-Furan-2-yl-5-(1-quinolin-2-ylmethyl-hexahydro-pyrrolo[3,4-b]pyrrol-5-yl)-[1,2,4]triazolo[1,5-a][1,3,5]triazin-7-ylamine | 454 [M + H]+ | Ex. 16 |

-continued

| Example | Compound Name | Mass Spec. (m/z) | Synthetic Method |
|---------|---------------|------------------|------------------|
| Ex. 150 | 7-[5-(2,3-Dichloro-6-fluoro-benzyl)-2,5-diaza-bicyclo[2.2.1]hept-2-yl]-2-furan-2-yl-[1,2,4]triazolo[1,5-c]pyrimidin-5-ylamine | 474 [M + H]+ | Ex. 18 |
| Ex. 151 | 7-[5-(2,4-Difluoro-benzyl)-2,5-diaza-bicyclo[2.2.1]hept-2-yl]-2-furan-2-yl-[1,2,4]triazolo[1,5-c]pyrimidin-5-ylamine | 424 [M + H]+ | Ex. 18 |
| Ex. 152 | 7-[5-(5-Bromo-furan-2-ylmethyl)-2,5-diaza-bicyclo[2.2.1]hept-2-yl]-2-furan-2-yl-[1,2,4]triazolo[1,5-c]pyrimidin-5-ylamine | 456 [M + H]+ | Ex. 18 |
| Ex. 153 | 2-Furan-2-yl-7-(5-quinolin-2-ylmethyl-2,5-diaza-bicyclo[2.2.1]hept-2-yl)-[1,2,4]triazolo[1,5-c]pyrimidin-5-ylamine | 439 [M + H]+ | Ex. 18 |

The $A_{2a}$ modulating activity of compounds of the present invention can be assessed by methods described in the following examples.

EXAMPLE 154

Numerous compounds of the present invention were prepared (see working examples and table above) and tested. Specifically, the $K_i$ values for rat and human $A_1$ adenosine receptors and for human $A_{2a}$ adenosine receptors were determined according to the following binding assay protocol. The ratio $A_{2a}/A_1$ was also calculated.

Materials

Adenosine deaminase and HEPES were purchased from Sigma-Aldrich (St. Louis, Mo.). Ham's F-12 cell culture medium and fetal bovine serum were purchased from GIBCO Life Technologies (Gaithersburg, Md.). Antibiotic G-418, Falcon 150 mM culture plates and Costar 12-well culture plates were purchased from Fisher (Pittsburgh, Pa.). [$^3$H] CPX was purchased from DuPont-New England Nuclear Research Products (Boston, Mass.). Penicillin/streptomycin antibiotic mixture was purchased from Mediatech (Washington, D.C.). The composition of HEPES-buffered Hank's solution was: 130 mM NaCl, 5.0 mM Cl, 1.5 mM CaCl$_2$, 0.41 mM MgSO$_4$, 0.49 mM Na$_2$HPO$_4$, 0.44 mM KH$_2$PO$_4$, 5.6 mM dextrose, and 5 mM HEPES (pH 7.4).

Membrane Preparation $A_{2a}$ Receptor: Membranes were prepared from rat brain tissues purchased from Pel-Freez (Brown Deer, Wis.). Tissues were homogenized in buffer A (10 mM EDTA, 10 mM Na-HEPES, pH 7.4) supplemented with protease inhibitors (10 μg/ml benzamidine, 100 μM PMSF, and 2 μg/ml each of aprotinin, pepstatin and leupeptin), and centrifuged at 20,000×g for 20 minutes. Pellets were resuspended and washed twice with buffer HE (10 mM Na-HEPES, 1 mM EDTA, pH 7.4, plus protease inhibitors). Final pellets were resuspended in buffer HE, supplemented with 10% (w/v) sucrose and protease inhibitors, and frozen in aliquots at −80° C. Protein concentrations were measured using BCA protein assay kit (Pierce, Rockford, Ill.).

$A_1$ Receptor: Membranes were prepared from rat cerebral cortex isolated from freshly euthanized rats. Tissues were homogenized in buffer A (10 mM EDTA, 01 mM Na-HEPES, pH 7.4) supplemented with protease inhibitors (10 μg/ml benzamidine, 100 μM PMSF, and 2 μg/ml each of aprotinin, pepstatin and leupeptin), and centrifuged at 20,000×g for 20 minutes. Pellets were resuspended and washed twice with buffer HE (10 mM Na-HEPES, 1 mM EDTA, pH 7.4, plus protease inhibitors). Final pellets were resuspended in buffer HE, supplemented with 10% (w/v) sucrose and protease inhibitors, and frozen in aliquots at −80° C. Protein concentrations were measured using BCA protein assay kit (Pierce).

Radioligand Binding Assays

Membranes (40-70 μg membrane protein), radioligands and varying concentrations of test compounds of the present invention were incubated in triplicates in 0.1 ml buffer HE plus 2 units/ml adenosine deaminase for 2.5 hours at 21° C. Radioligand [$^3$H]DPCPX was used for competition binding assays on $A_1$ receptors and [$^3$H]ZM241385 was used for $A_{2a}$ adenosine receptors. Nonspecific binding was measured in the presence of 10 μM NECA for $A_1$ receptors, or 10 μM XAC for $A_{2a}$ receptors. Binding assays were terminated by filtration over Whatman GF/C glass fiber filters using a BRANDEL cell harvester. Filters were rinsed three times with 3-4 mL ice cold 10 mM Tris-HCl, pH 7.4 and 5 mM MgCl$_2$ at 4° C., and were counted in a Wallac β-counter.

Analysis of Binding Data $K_i$ determination: Competition binding data were fit to a single-site binding model and plotted using Prizm GraphPad. Cheng-Prusoff equation $K_i=IC_{50}/(1+[I]/K_d)$ was used to calculate $K_i$ values from $IC_{50}$ values, where $K_i$ is the affinity constant for the competing test compound, [I] is the concentration of the free radioligand; and $K_d$ is the affinity constant for the radioligand.

$A_{2a}$% binding: Data were generally expressed as percentage of total specific binding at 1 μM of competing test compound (% total specific binding)=100%×(specific binding with 1 μM of competing test compound/total specific binding).

Results

Compounds of formula (I) typically exhibited $K_i$ values of less than 10 μM and $A_{2a}$% binding ranging from 1% to 50%; some compounds exhibited $K_i$ values of less than 1 μM.

EXAMPLE 155

Catalepsy Experiments

Haloperidol-induced catalepsy was used to mimic the effects of Parkinson's disease in rats and mice. Animals were injected with haloperidol, which causes immobility. A test compound of the present invention was then administered orally and the compound's ability to reverse these Parkinson's-like symptoms was analyzed. For reference, see Sanberg et al., Behavioral Neuroscience 102: 748-759 (1988).

Rats

Male Sprague-Dawley rats (225-275 g) were injected with haloperidol (1 mg/kg s.c.) to induce catalepsy. These rats were then subjected to the bar test. In this test, the rats' forelimbs were placed on an aluminum bar (1 cm in diameter) suspended horizontally 10 cm above the surface of the bench. The elapsed time until the rat placed one forepaw back on the bench was measured, with a maximum time of 120 seconds allowed. It should be noted that these rats were in a cataleptic state and therefore were unable to correct an externally imposed posture (i.e., the cataleptic rats, when placed in this unnatural position, were unable to come down from the horizontal bar over a period of 120 seconds or more). Once the rats showed a stable baseline cataleptic response (about three hours after haloperidol injection), a test compound of the present invention or vehicle alone is administered orally, and catalepsy data from the bar test were measured every 30 minutes for the next 3 hours. Data were analyzed by one factor analysis of variance with Dunnett's 't' test used to make post-hoc comparisons. Many compounds of this invention showed oral activity at a dosage of 10 mg/kg or lower, which allowed the cataleptic animals to come down from the bar within 60 seconds and remained in a catalepsy-free state for at least 60 minutes Mice Mice catalepsy experiment was conducted in the same manner as described above except mice (CD-1; 25-30 g) were used instead of rats, the dose of haloperidol was 3 mg/kg s.c. instead of 1 mg/kg s.c., and the bar was suspended 4.5 cm instead of 10 cm above the surface of the bench. Many compounds of this invention showed oral activity at a dosage of 10 mg/kg or lower, which allowed the cataleptic animals to come down from the bar within 60 seconds and remained in a catalepsy-free state for at least 60 minutes.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of the following formula:

(I)

or a pharmaceutically acceptable salt or N-oxide thereof; wherein
- A is an aryl or heteroaryl;
- each of B, $B^1$, and $B^2$ is N;
- each of $R^2$ and $R^3$ is independently hydrogen, alkyl, cycloalkyl, cycloalkenyl, aryl, aralkyl, heterocycloalkyl, heterocycloalkenyl, heteroaryl, or heteroaralkyl;
- $X^1$ is a bond or $C_{1-6}$ alkylene, $C_{2-6}$ alkenylene, or $C_{2-6}$ alkynylene, each of which being optionally interrupted by or linked terminally to —O—, —S—, or —N($R^2$)—;
- $X^2$ is a bond, $C_{1-6}$ alkylene, $C_{2-6}$ alkenylene, or $C_{2-6}$ alkynylene;
- L is a linker selected from the group consisting of:

wherein:
- each of R' and R" is independently hydrogen, alkyl, alkenyl, alkynyl, alkoxy, acyl, halo, hydroxy, amino, nitro, oxo, thioxo, cyano, guanadino, amidino, carboxy, sulfo, sulfoxy, mercapto, alkylsulfanyl, alkylsulfinyl, alkylsulfonyl, aminocarbonyl, alkylcarbonylamino, alkylsulfonylamino, alkoxycarbonyl, alkylcarbonyloxy, urea, thiourea, sulfamoyl, sulfamide, carbamoyl, cycloalkyl, cycloalkyloxy, cycloalkylsulfanyl, heterocycloalkyl, heterocycloalkyloxy, heterocycloalkylsulfanyl, aryl, aryloxy, arylsulfanyl, aroyl, heteroaryl, heteroaryloxy, heteroarylsulfanyl, or heteroaroyl;
- X is —C($R^2$)($R^3$)—, —N($R^2$)—, —O—, or —S—;
- each of p, p1 and p2 is independently 0-2;
- each of q1 and q2 is independently 0-2;
- each of m1 and m2 is independently 0-2;
- each of r and r1 is independently is 1-2; and
- r2 is 0-1;
- Y is —C($R^2$)($R^3$)—, —N(R''')—, —O—, —S—, —SO—, —SO$_2$—, —CO—, —CO$_2$—, or a bond where R''' is hydrogen, alkyl, alkenyl, alkynyl, cycloalkyl, cycloalkylalkyl, cycloalkenyl, cycloalkenylalkyl, aryl, aralkyl, heterocyclyl, or heterocyclylalkyl; and
- $R^1$ is hydrogen, alkyl, alkenyl, alkynyl, cycloalkyl, cycloalkylalkyl, cycloalkenyl, cycloalkenylalkyl, aryl, aralkyl, heterocyclyl, or heterocyclylalkyl.

2. The compound of claim 1, wherein L is

-continued

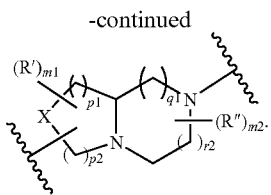

3. The compound of claim 2, wherein L is

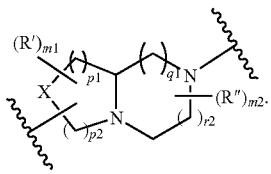

4. The compound of claim 3, wherein X is —CH$_2$—, p1 is 1, p2 is 1 or 2, q1 is 1, r2 is 1 or 2, each of m1 and m2 is independently 0 or 1, and each of R' and R" is independently hydrogen or alkyl.

5. The compound of claim 4, wherein L is

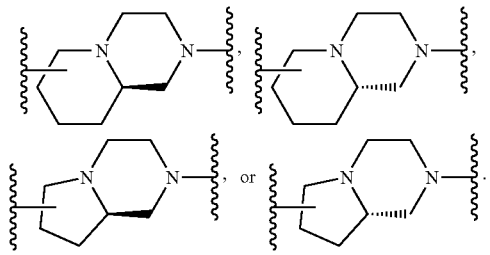

6. The compound of claim 2, wherein L is

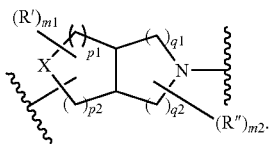

7. The compound of claim 6, wherein X is —CH$_2$—, p1 is 0 or 1, p2 is 1 or 2, q1 is 1, q2 is 1 or 2, each of m1 and m2 is independently 0 or 1, and each of R' and R" is independently hydrogen or alkyl.

8. The compound of claim 7, wherein L is

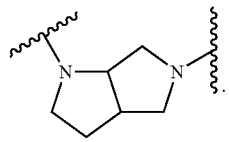

9. The compound of claim 2, wherein X$^1$ is a bond or C$_{1-4}$ alkylene that is optionally linked terminally to —N(R$^2$)—, where R$^2$ is hydrogen or alkyl.

10. The compound of claim 2, wherein X$^2$ is a bond or C$_{1-4}$ alkylene.

11. The compound of claim 2, wherein Y is —N(R''')—, —O—, —S—, or a bond where R''' is hydrogen, alkyl, cycloalkyl, cycloalkylalkyl, aryl, aralkyl, heterocyclyl, or heterocyclylalkyl.

12. The compound of claim 11, wherein R''' is hydrogen, cycloalkylalkyl, heterocycloalkylalkyl, aryl, heteroaryl, aralkyl, or heteroaralkyl.

13. The compound of claim 2, wherein each of R$^2$ and R$^3$ is independently hydrogen or alkyl.

14. The compound of claim 2, wherein R$^1$ is hydrogen, alkyl, cycloalkyl, cycloalkylalkyl, aryl, aralkyl, heterocyclyl, or heterocyclylalkyl.

15. The compound of claim 2, wherein R$^1$ is hydrogen, or R$^1$ is phenyl, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, triazinyl, quinolinyl, isoquinolinyl, indolyl, isoindolyl, benzofuryl, benzothiophenyl, benzimidazolyl, benzthiazolyl, furopyridyl, or thienopyridyl; each of which being optionally substituted with C$_{1-4}$ alkyl, halo, hydroxy, C$_{1-4}$ alkoxy, or C$_{1-4}$ alkylthio.

16. The compound of claim 2, wherein A is heteroaryl.

17. The compound of claim 3, wherein X$^1$ is a bond or C$_{1-4}$ alkylene that is optionally linked terminally to —N(R$^2$)—; X$^2$ is a bond or C$_{1-4}$ alkylene; Y is —N(R''')—, —O—, —S—, or a bond where R''' is hydrogen, cycloalkylalkyl, heterocycloalkylalkyl, aryl, heteroaryl, aralkyl, or heteroaralkyl; each of R$^2$ and R$^3$ is independently hydrogen or alkyl; R$^1$ is cycloalkyl, cycloalkylalkyl, aryl, aralkyl, heterocyclyl, or heterocyclylalkyl; and A is heteroaryl.

18. The compound of claim 17, wherein X$^1$ is a bond; each of R$^2$ and R$^3$ is hydrogen; and R$^1$ is aryl or heteroaryl.

19. The compound of claim 17, wherein X is —CH$_2$—, p1 is 1, p2 is 1 or 2, q1 is 1, r2 is 1 or 2, each of m1 and m2 is independently 0 or 1, and each of R' and R" is independently hydrogen or alkyl.

20. The compound of claim 6, wherein X$^1$ is a bond or C$_{1-4}$ alkylene that is optionally linked terminally to —N(R$^2$)— where R$^2$ is hydrogen or alkyl; X$^2$ is a bond or C$_{1-4}$ alkylene; Y is —N(R''')—, —O—, —S—, or a bond where R''' is hydrogen, cycloalkylalkyl, heterocycloalkylalkyl, aryl, heteroaryl, aralkyl, or heteroaralkyl; each of R$^2$ and R$^3$ is independently hydrogen or alkyl; R$^1$ is cycloalkyl, cycloalkylalkyl, aryl, aralkyl, heterocyclyl, or heterocyclylalkyl; and A is heteroaryl.

21. The compound of claim 20, wherein X is —CH$_2$—, p1 is 0 or 1, p2 is 1 or 2, q1 is 1, q2 is 1 or 2, each of m1 and m2 is independently 0 or 1, and each of R' and R" is independently hydrogen or alkyl.

22. The compound of claim 1, said compound being selected from the group consisting of:
(7RS, 9aRS)-[2-(7-amino-2-furan-2-yl-[1,2,4]triazolo[1,5-a][1,3,5]triazin-5-yl)-octahydro-pyrido[1,2-a]pyrazin-7-yl]-methanol;
(6RS, 9aRS)-[2-(7-amino-2-furan-2-yl-[1,2,4]triazolo[1,5-a][1,3,5]triazin-5-yl)-octahydro-pyrido[1,2-a]pyrazin-6-yl]-methanol;
(7RS, 9aRS)-[2-(5-amino-2-furan-2-yl-[1,2,4]triazolo[1,5-c]pyrimidin-7-yl)-octahydro-pyrido[1,2-a]pyrazin-7-yl]-methanol;
(7RS, 9aRS)-[2-(7-amino-2-furan-2-yl-[1,2,4]triazolo[1,5-a]pyrimidin-5-yl)-octahydro-pyrido[1,2-a]pyrazin-7-yl]-methanol;

(7RS, 9aSR)-5-[7-(3-fluoro-phenoxymethyl)-octahydro-pyrido[1,2-a]pyrazin-2-yl]-2-furan-2-yl-[1,2,4]triazolo[1,5-a][1,3,5]triazin-7-ylamine;

(7RS, 9aRS)-2-furan-2-yl-N$^5$-(2-pyrimidin-2-yl-octahydro-pyrido[1,2-a]pyrazin-7-ylmethyl)-[1,2,4]triazolo[1,5-a][1,3,5]triazine-5,7-diamine;

(7RS, 9aSR)—N$^5$-[2-(5-chloro-1-methyl-3-trifluoromethyl-1H-pyrazol-4-ylmethyl)-octahydro-pyrido[1,2-a]pyrazin-7-ylmethyl]-2-furan-2-yl-[1,2,4]triazolo[1,5-a][1,3,5]triazine-5,7-diamine;

(7RS, 9aSR)-2-furan-2-yl-N$^5$-(2-pyrimidin-2-yl-octahydro-pyrido[1,2-a]pyrazin-7-ylmethyl)-[1,2,4]triazolo[1,5-a][1,3,5]triazine-5,7-diamine;

(7RS, 9aRS)-5-(7-aminomethyl-octahydro-pyrido[1,2-a]pyrazin-2-yl)-2-furan-2-yl-[1,2,4]triazolo[1,5-a][1,3,5]triazin-7-ylamine;

(7RS, 9aRS)-5-{7-[(bis-pyridin-4-ylmethyl-amino)-methyl]-octahydro-pyrido[1,2-a]pyrazin-2-yl}-2-furan-2-yl-[1,2,4]triazolo[1,5-a][1,3,5]triazin-7-ylamine;

(7RS, 9aRS)-2-furan-2-yl-5-[7-(pyrimidin-2-ylaminomethyl)-octahydro-pyrido[1,2-a]pyrazin-2-yl]-[1,2,4]triazolo[1,5-a][1,3,5]triazin-7-ylamine;

(7RS, 9aRS)-2-furan-2-yl-5-(7-{[(pyridin-4-ylmethyl)-amino]-methyl}-octahydro-pyrido[1,2-a]pyrazin-2-yl)-[1,2,4]triazolo[1,5-a][1,3,5]triazin-7-ylamine;

2-furan-2-yl-5-[5-(5-methyl-isoxazol-3-ylmethyl)-2,5-diaza-bicyclo[2.2.1]hept-2-yl]-[1,2,4]triazolo[1,5-a][1,3,5]triazin-7-ylamine;

5-[5-(4-fluoro-benzyl)-2,5-diaza-bicyclo[2.2.1]hept-2-yl]-2-furan-2-yl-[1,2,4]triazolo[1,5-a][1,3,5]triazin-7-ylamine;

5-[5-(4-chloro-benzyl)-hexahydro-pyrrolo[3,4-b]pyrrol-1-yl]-2-furan-2-yl-[1,2,4]triazolo[1,5-a][1,3,5]triazin-7-ylamine;

5-[1-(2,6-dichloro-benzyl)-hexahydro-pyrrolo[3,4-b]pyrrol-5-yl]-2-furan-2-yl-[1,2,4]triazolo[1,5-a][1,3,5]triazin-7-ylamine;

(±)-2-furan-2-yl-5-(octahydro-pyrido[1,2-a]pyrazin-2-yl)-[1,2,4]triazolo[1,5-a][1,3,5]triazin-7-ylamine;

(±)-2-furan-2-yl-5-(hexahydro-pyrrolo[1,2-a]pyrazin-2-yl)-[1,2,4]triazolo[1,5-a][1,3,5]triazin-7-ylamine;

(S)-2-furan-2-yl-5-(hexahydro-pyrrolo[1,2-a]pyrazin-2-yl)-[1,2,4]triazolo[1,5-a][1,3,5]triazin-7-ylamine;

(3S,8aS)-5-(3-benzyl-hexahydro-pyrrolo[1,2-a]pyrazin-2-yl)-2-furan-2-yl-[1,2,4]triazolo[1,5-a][1,3,5]triazin-7-ylamine;

(7RS, 9aSR)-[2-(7-amino-2-furan-2-yl-[1,2,4]triazolo[1,5-a][1,3,5]triazin-5-yl)-octahydro-pyrido[1,2-a]pyrazin-7-yl]-methanol;

(7RS, 9aRS)-5-[7-(2,4-difluoro-phenoxymethyl)-octahydro-pyrido[1,2-a]pyrazin-2-yl]-2-furan-2-yl-[1,2,4]triazolo[1,5-a][1,3,5]triazin-7-ylamine;

(7RS, 9aRS)-2-furan-2-yl-5-[7-(quinolin-6-yloxymethyl)-octahydro-pyrido[1,2-a]pyrazin-2-yl]-[1,2,4]triazolo[1,5-a][1,3,5]triazin-7-ylamine;

(7RS, 9aRS)-2-furan-2-yl-5-(7-phenoxymethyl-octahydro-pyrido[1,2-a]pyrazin-2-yl)-[1,2,4]triazolo[1,5-a][1,3,5]triazin-7-ylamine;

(7RS, 9aRS)-2-furan-2-yl-5-[7-(5,6,7,8-tetrahydro-naphthalen-2-yloxymethyl)-octahydro-pyrido[1,2-a]pyrazin-2-yl]-[1,2,4]triazolo[1,5-a][1,3,5]triazin-7-ylamine;

(7RS, 9aRS)-5-[7-(2-fluoro-phenoxymethyl)-octahydro-pyrido[1,2-a]pyrazin-2-yl]-2-furan-2-yl-[1,2,4]triazolo[1,5-a][1,3,5]triazin-7-ylamine;

(7RS, 9aRS)-5-[7-(3-fluoro-phenoxymethyl)-octahydro-pyrido[1,2-a]pyrazin-2-yl]-2-furan-2-yl-[1,2,4]triazolo[1,5-a][1,3,5]triazin-7-ylamine;

(7RS, 9aRS)-5-[7-(4-fluoro-phenoxymethyl)-octahydro-pyrido[1,2-a]pyrazin-2-yl]-2-furan-2-yl-[1,2,4]triazolo[1,5-a][1,3,5]triazin-7-ylamine;

(7RS, 9aRS)-2-furan-2-yl-5-[7-(4-methoxy-phenoxymethyl)-octahydro-pyrido[1,2-a]pyrazin-2-yl]-[1,2,4]triazolo[1,5-a][1,3,5]triazin-7-ylamine;

(7RS, 9aRS)-2-furan-2-yl-5-[7-(2,3,5-trifluoro-phenoxymethyl)-octahydro-pyrido[1,2-a]pyrazin-2-yl]-[1,2,4]triazolo[1,5-a][1,3,5]triazin-7-ylamine;

(7RS, 9aRS)-2-furan-2-yl-5-[7-(2,4,6-trifluoro-phenoxymethyl)-octahydro-pyrido[1,2-a]pyrazin-2-yl]-[1,2,4]triazolo[1,5-a][1,3,5]triazin-7-ylamine;

(7RS, 9aRS)-2-furan-2-yl-5-[7-(pyridin-2-yloxymethyl)-octahydro-pyrido[1,2-a]pyrazin-2-yl]-[1,2,4]triazolo[1,5-a][1,3,5]triazin-7-ylamine;

(7RS, 9aRS)-2-furan-2-yl-5-[7-(pyridin-3-yloxymethyl)-octahydro-pyrido[1,2-a]pyrazin-2-yl]-[1,2,4]triazolo[1,5-a][1,3,5]triazin-7-ylamine;

(7RS, 9aRS)-2-furan-2-yl-5-[7-(pyridin-4-yloxymethyl)-octahydro-pyrido[1,2-a]pyrazin-2-yl]-[1,2,4]triazolo[1,5-a][1,3,5]triazin-7-ylamine;

(7RS, 9aRS)-2-furan-2-yl-5-[7-(4-trifluoromethyl-pyrimidin-2-yloxymethyl)-octahydro-pyrido[1,2-a]pyrazin-2-yl]-[1,2,4]triazolo[1,5-a][1,3,5]triazin-7-ylamine;

(7RS, 9aRS)-2-furan-2-yl-5-[7-(6-trifluoromethyl-pyrimidin-4-yloxymethyl)-octahydro-pyrido[1,2-a]pyrazin-2-yl]-[1,2,4]triazolo[1,5-a][1,3,5]triazin-7-ylamine;

(7RS, 9aRS)-2-furan-2-yl-5-[7-(quinazolin-2-yloxymethyl)-octahydro-pyrido[1,2-a]pyrazin-2-yl]-[1,2,4]triazolo[1,5-a][1,3,5]triazin-7-ylamine;

(7RS, 9aRS)-2-furan-2-yl-5-[7-(isoquinolin-3-yloxymethyl)-octahydro-pyrido[1,2-a]pyrazin-2-yl]-[1,2,4]triazolo[1,5-a][1,3,5]triazin-7-ylamine;

(7RS, 9aRS)-2-furan-2-yl-5-[7-(isoquinolin-5-yloxymethyl)-octahydro-pyrido[1,2-a]pyrazin-2-yl]-[1,2,4]triazolo[1,5-a][1,3,5]triazin-7-ylamine;

(7RS, 9aRS)-2-furan-2-yl-5-[7-(1H-pyrazolo[3,4-d]pyrimidin-4-yloxymethyl)-octahydro-pyrido[1,2-a]pyrazin-2-yl]-[1,2,4]triazolo[1,5-a][1,3,5]triazin-7-ylamine;

(7RS, 9aRS)-2-furan-2-yl-5-(7-imidazol-1-ylmethyl-octahydro-pyrido[1,2-a]pyrazin-2-yl)-[1,2,4]triazolo[1,5-a][1,3,5]triazin-7-ylamine;

(7RS, 9aRS)-2-furan-2-yl-5-(7-[1,2,4]triazol-1-ylmethyl-octahydro-pyrido[1,2-a]pyrazin-2-yl)-[1,2,4]triazolo[1,5-a][1,3,5]triazin-7-ylamine;

(7RS, 9aRS)-2-furan-2-yl-5-(7-tetrazol-1-ylmethyl-octahydro-pyrido[1,2-a]pyrazin-2-yl)-[1,2,4]triazolo[1,5-a][1,3,5]triazin-7-ylamine;

(7RS, 9aSR)-5-[7-(2,4-difluoro-phenoxymethyl)-octahydro-pyrido[1,2-a]pyrazin-2-yl]-2-furan-2-yl-[1,2,4]triazolo[1,5-a][1,3,5]triazin-7-ylamine;

(7RS, 9aSR)-2-furan-2-yl-5-[7-(4-methoxy-phenoxymethyl)-octahydro-pyrido[1,2-a]pyrazin-2-yl]-[1,2,4]triazolo[1,5-a][1,3,5]triazin-7-ylamine;

(7RS, 9aSR)-2-furan-2-yl-5-(7-phenoxymethyl-octahydro-pyrido[1,2-a]pyrazin-2-yl)-[1,2,4]triazolo[1,5-a][1,3,5]triazin-7-ylamine;

(7RS, 9aSR)-2-furan-2-yl-5-[7-(5,6,7,8-tetrahydro-naphthalen-2-yloxymethyl)-octahydro-pyrido[1,2-a]pyrazin-2-yl]-[1,2,4]triazolo[1,5-a][1,3,5]triazin-7-ylamine;

(7RS, 9aSR)-2-furan-2-yl-5-[7-(pyridin-2-yloxymethyl)-octahydro-pyrido[1,2-a]pyrazin-2-yl]-[1,2,4]triazolo[1,5-a][1,3,5]triazin-7-ylamine;

(7RS, 9aSR)-2-furan-2-yl-5-[7-(pyridin-3-yloxymethyl)-octahydro-pyrido[1,2-a]pyrazin-2-yl]-[1,2,4]triazolo[1,5-a][1,3,5]triazin-7-ylamine;

(7RS, 9aSR)-2-furan-2-yl-5-[7-(pyridin-4-yloxymethyl)-octahydro-pyrido[1,2-a]pyrazin-2-yl]-[1,2,4]triazolo[1,5-a][1,3,5]triazin-7-ylamine;

(7RS, 9aSR)-5-[7-(benzo[1,3]dioxol-5-yloxymethyl)-octahydro-pyrido[1,2-a]pyrazin-2-yl]-2-furan-2-yl-[1,2,4]triazolo[1,5-a][1,3,5]triazin-7-ylamine;

(7RS, 9aSR)-2-furan-2-yl-5-[7-(quinazolin-2-yloxymethyl)-octahydro-pyrido[1,2-a]pyrazin-2-yl]-[1,2,4]triazolo[1,5-a][1,3,5]triazin-7-ylamine;

(7RS, 9aSR)-2-furan-2-yl-5-[7-(quinolin-2-yloxymethyl)-octahydro-pyrido[1,2-a]pyrazin-2-yl]-[1,2,4]triazolo[1,5-a][1,3,5]triazin-7-ylamine;

(7RS, 9aSR)-2-furan-2-yl-5-[7-(isoquinolin-3-yloxymethyl)-octahydro-pyrido[1,2-a]pyrazin-2-yl]-[1,2,4]triazolo[1,5-a][1,3,5]triazin-7-ylamine;

(7RS, 9aSR)-2-furan-2-yl-5-[7-(isoquinolin-5-yloxymethyl)-octahydro-pyrido[1,2-a]pyrazin-2-yl]-[1,2,4]triazolo[1,5-a][1,3,5]triazin-7-ylamine;

(7RS, 9aSR)-5-[7-(2-fluoro-phenoxymethyl)-octahydro-pyrido[1,2-a]pyrazin-2-yl]-2-furan-2-yl-[1,2,4]triazolo[1,5-a][1,3,5]triazin-7-ylamine;

(7RS, 9aSR)-5-[7-(4-fluoro-phenoxymethyl)-octahydro-pyrido[1,2-a]pyrazin-2-yl]-2-furan-2-yl-[1,2,4]triazolo[1,5-a][1,3,5]triazin-7-ylamine;

(6RS, 9aRS)-[2-furan-2-yl-5-(6-phenoxymethyl-octahydro-pyrido[1,2-a]pyrazin-2-yl)-[1,2,4]triazolo[1,5-a][1,3,5]triazin-7-ylamine;

(6RS, 9aRS)-[2-furan-2-yl-5-[6-(5,6,7,8-tetrahydro-naphthalen-1-yloxymethyl)-octahydro-pyrido[1,2-a]pyrazin-2-yl]-[1,2,4]triazolo[1,5-a][1,3,5]triazin-7-ylamine;

(6RS, 9aRS)-[5-[6-(3-amino-phenoxymethyl)-octahydro-pyrido[1,2-a]pyrazin-2-yl]-2-furan-2-yl-[1,2,4]triazolo[1,5-a][1,3,5]triazin-7-ylamine;

(6RS, 9aRS)-[5-[6-(benzo[1,3]dioxol-5-yloxymethyl)-octahydro-pyrido[1,2-a]pyrazin-2-yl]-2-furan-2-yl-[1,2,4]triazolo[1,5-a][1,3,5]triazin-7-ylamine;

(6RS, 9aRS)-[2-furan-2-yl-5-[6-(1H-indol-5-yloxymethyl)-octahydro-pyrido[1,2-a]pyrazin-2-yl]-[1,2,4]triazolo[1,5-a][1,3,5]triazin-7-ylamine;

(6RS, 9aRS)-1-[2-(7-amino-2-furan-2-yl-[1,2,4]triazolo[1,5-a][1,3,5]triazin-5-yl)-octahydro-pyrido[1,2-a]pyrazin-6-ylmethyl]-1H-indol-5-ol;

(7RS, 9aRS)-3-amino-5-{7-[(7-amino-2-furan-2-yl-[1,2,4]triazolo[1,5-a][1,3,5]triazin-5-ylamino)-methyl]-octahydro-pyrido[1,2-a]pyrazin-2-yl}-6-chloro-pyrazine-2-carboxylic acid methyl ester;

(7RS, 9aRS)—N-5-[2-(3,5-difluoro-phenyl)-octahydro-pyrido[1,2-a]pyrazin-7-ylmethyl]-2-furan-2-yl-[1,2,4]triazolo[1,5-a][1,3,5]triazine-5,7-diamine;

(7RS, 9aRS)—N-5-[2-(2,4-difluoro-benzyl)-octahydro-pyrido[1,2-a]pyrazin-7-ylmethyl]-2-furan-2-yl-[1,2,4]triazolo[1,5-a][1,3,5]triazine-5,7-diamine;

(7RS, 9aSR)-5-(7-aminomethyl-octahydro-pyrido[1,2-a]pyrazin-2-yl)-2-furan-2-yl-[1,2,4]triazolo[1,5-a][1,3,5]triazin-7-ylamine;

(7RS, 9aRS)-5-(7-{[bis-(2-fluoro-benzyl)-amino]-methyl}-octahydro-pyrido[1,2-a]pyrazin-2-yl)-2-furan-2-yl-[1,2,4]triazolo[1,5-a][1,3,5]triazin-7-ylamine;

(7RS, 9aRS)-5-(7-{[bis-(2,4-difluoro-benzyl)-amino]-methyl}-octahydro-pyrido[1,2-a]pyrazin-2-yl)-2-furan-2-yl-[1,2,4]triazolo[1,5-a][1,3,5]triazin-7-ylamine;

(7RS, 9aRS)-5-{7-[(2,4-difluoro-benzylamino)-methyl]-octahydro-pyrido[1,2-a]pyrazin-2-yl}-2-furan-2-yl-[1,2,4]triazolo[1,5-a][1,3,5]triazin-7-ylamine;

(7RS, 9aRS)-5-(7-{[bis-(2,4,6-trifluoro-benzyl)-amino]-methyl}-octahydro-pyrido[1,2-a]pyrazin-2-yl)-2-furan-2-yl-[1,2,4]triazolo[1,5-a][1,3,5]triazin-7-ylamine;

(7RS, 9aRS)-5-(7-{[bis-(2,3-difluoro-benzyl)-amino]-methyl}-octahydro-pyrido[1,2-a]pyrazin-2-yl)-2-furan-2-yl-[1,2,4]triazolo[1,5-a][1,3,5]triazin-7-ylamine;

(7RS, 9aRS)-5-(7-{[bis-(2,6-difluoro-benzyl)-amino]-methyl}-octahydro-pyrido[1,2-a]pyrazin-2-yl)-2-furan-2-yl-[1,2,4]triazolo[1,5-a][1,3,5]triazin-7-ylamine;

(7RS, 9aRS)-5-(7-{[bis-(3,5-difluoro-benzyl)-amino]-methyl}-octahydro-pyrido[1,2-a]pyrazin-2-yl)-2-furan-2-yl-[1,2,4]triazolo[1,5-a][1,3,5]triazin-7-ylamine;

(7RS, 9aRS)-5-(7-{[bis-(5-chloro-furan-2-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine;

(7RS, 9aRS)-5-{7-[(bis-pyridin-2-ylmethyl-amino)-methyl]-octahydro-pyrido[1,2-a]pyrazin-2-yl}-2-furan-2-yl-[1,2,4]triazolo[1,5-a][1,3,5]triazin-7-ylamine;

(7RS, 9aRS)-5-{7-[(bis-pyridin-3-ylmethyl-amino)-methyl]-octahydro-pyrido[1,2-a]pyrazin-2-yl}-2-furan-2-yl-[1,2,4]triazolo[1,5-a][1,3,5]triazin-7-ylamine;

(7RS, 9aRS)-2-furan-2-yl-5-(7-{[(pyridin-3-ylmethyl)-amino]-methyl}-octahydro-pyrido[1,2-a]pyrazin-2-yl)-[1,2,4]triazolo[1,5-a][1,3,5]triazin-7-ylamine;

(7RS, 9aRS)-5-(7-{[bis-(2-chloro-1-methyl-4-trifluoromethyl-1H-pyrrol-3-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine;

(7RS, 9aRS)-5-(7-{[bis-(3,5-dimethyl-isoxazol-4-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine;

(7RS, 9aRS)-5-(7-{[(3,5-dimethyl-isoxazol-4-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine;

(7RS, 9aRS)-5-{7-[(bis-cyclohexylmethyl-amino)-methyl]-octahydro-pyrido[1,2-a]pyrazin-2-yl}-2-furan-2-yl-[1,2,4]triazolo[1,5-a][1,3,5]triazin-7-ylamine;

(7RS, 9aRS)-5-{7-[(bis-furan-2-ylmethyl-amino)-methyl]-octahydro-pyrido[1,2-a]pyrazin-2-yl}-2-furan-2-yl-[1,2,4]triazolo[1,5-a][1,3,5]triazin-7-ylamine;

(7RS, 9aRS)-5-(7-{[bis-(1H-pyrrol-2-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine;

(7RS, 9aRS)-5-(7-{[bis-(5-chloro-1,3-dimethyl-1H-pyrazol-4-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine;

(7RS, 9aRS)-5-(7-{[(5-chloro-1,3-dimethyl-1H-pyrazol-4-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine;

(7RS, 9aRS)-5-{7-[(bis-thiazol-2-ylmethyl-amino)-methyl]-octahydro-pyrido[1,2-a]pyrazin-2-yl}-2-furan-2-yl-[1,2,4]triazolo[1,5-a][1,3,5]triazin-7-ylamine;

(7RS, 9aRS)-5-{7-[(bis-thiophen-2-ylmethyl-amino)-methyl]-octahydro-pyrido[1,2-a]pyrazin-2-yl}-2-furan-2-yl-[1,2,4]triazolo[1,5-a][1,3,5]triazin-7-ylamine;

(7RS, 9aRS)-5-(7-{[bis-(5-methyl-thiophen-2-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine;

(7RS, 9aSR)-2-furan-2-yl-5-[7-(pyrimidin-2-ylaminomethyl)-octahydro-pyrido[1,2-a]pyrazin-2-yl]-[1,2,4]triazolo[1,5-a][1,3,5]triazin-7-ylamine;

(7RS, 9aSR)-5-{7-[(bis-pyridin-4-ylmethyl-amino)-methyl]-octahydro-pyrido[1,2-a]pyrazin-2-yl}-2-furan-2-yl-[1,2,4]triazolo[1,5-a][1,3,5]triazin-7-ylamine;

(7RS, 9aSR)-2-furan-2-yl-5-(7-{[(pyridin-4-ylmethyl)-amino]-methyl}-octahydro-pyrido[1,2-a]pyrazin-2-yl)-[1,2,4]triazolo[1,5-a][1,3,5]triazin-7-ylamine;

(7RS, 9aSR)-5-{7-[(bis-pyridin-3-ylmethyl-amino)-methyl]-octahydro-pyrido[1,2-a]pyrazin-2-yl}-2-furan-2-yl-[1,2,4]triazolo[1,5-a][1,3,5]triazin-7-ylamine;

(7RS, 9aSR)-2-furan-2-yl-5-(7-{[(pyridin-3-ylmethyl)-amino]-methyl}-octahydro-pyrido[1,2-a]pyrazin-2-yl)-[1,2,4]triazolo[1,5-a][1,3,5]triazin-7-ylamine;

(7RS, 9aSR)-5-{7-[(bis-furan-2-ylmethyl-amino)-methyl]-octahydro-pyrido[1,2-a]pyrazin-2-yl}-2-furan-2-yl-[1,2,4]triazolo[1,5-a][1,3,5]triazin-7-ylamine;

(7RS, 9aSR)-2-furan-2-yl-5-(7-{[(furan-2-ylmethyl)-amino]-methyl}-octahydro-pyrido[1,2-a]pyrazin-2-yl)-[1,2,4]triazolo[1,5-a][1,3,5]triazin-7-ylamine;

(7RS, 9aSR)-5-(7-{[bis-(3,5-dimethyl-isoxazol-4-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine;

(7RS, 9aSR)-5-(7-{[(3,5-dimethyl-isoxazol-4-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine;

(R)-2-furan-2-yl-5-(hexahydro-pyrrolo[1,2-a]pyrazin-2-yl)-[1,2,4]triazolo[1,5-a][1,3,5]triazin-7-ylamine;

2-furan-2-yl-5-(1-quinolin-2-ylmethyl-hexahydro-pyrrolo[3,4-b]pyrrol-5-yl)-[1,2,4]triazolo[1,5-a][1,3,5]triazin-7-ylamine; and (7RS, 9aRS)-2-furan-2-yl-5-[7-(quinolin-7-yloxymethyl)-octahydro-pyrido[1,2-a]pyrazin-2-yl]-[1,2,4]triazolo[1,5-a][1,3,5]triazin-7-ylamine.

23. The compound of claim 1, said compound being selected from the group consisting of:

(±)2-furan-2-yl-5-(octahydro-pyrido[1,2-a]pyrazin-2-yl)-[1,2,4]triazolo[1,5-a][1,3,5]triazin-7-ylamine;

(±)2-furan-2-yl-5-(hexahydro-pyrrolo[1,2-a]pyrazin-2-yl)-[1,2,4]triazolo[1,5-a][1,3,5]triazin-7-ylamine;

(7RS, 9aRS)-[2-(7-amino-2-furan-2-yl-[1,2,4]triazolo[1,5-a][1,3,5]triazin-5-yl)-octahydro-pyrido[1,2-a]pyrazin-7-yl]-methanol;

(6RS, 9aRS)-[2-(7-amino-2-furan-2-yl-[1,2,4]triazolo[1,5-a][1,3,5]triazin-5-yl)-octahydro-pyrido[1,2-a]pyrazin-6-yl]-methanol;

(7RS,9aRS)-2-Furan-2-yl-5-[7-(quinolin-6-yloxymethyl)-octahydro-pyrido[1,2-a]pyrazin-2-yl]-[1,2,4]triazolo[1,5-a][1,3,5]triazin-7-ylamine;

(7RS,9aRS)-2-Furan-2-yl-5-(7-phenoxymethyl-octahydro-pyrido[1,2-a]pyrazin-2-yl)-[1,2,4]triazolo[1,5-a][1,3,5]triazin-7-ylamine;

(7RS,9aRS)-5-[7-(2-fluoro-phenoxymethyl)-octahydro-pyrido[1,2-a]pyrazin-2-yl]-2-furan-2-yl-[1,2,4]triazolo[1,5-a][1,3,5]triazin-7-ylamine;

(7RS,9aRS)-5-[7-(3-fluoro-phenoxymethyl)-octahydro-pyrido[1,2-a]pyrazin-2-yl]-2-furan-2-yl-[1,2,4]triazolo[1,5-a][1,3,5]triazin-7-ylamine;

(7RS,9aRS)-2-furan-2-yl-5-[7-(pyridin-3-yloxymethyl)-octahydro-pyrido[1,2-a]pyrazin-2-yl]-[1,2,4]triazolo[1,5-a][1,3,5]triazin-7-ylamine;

(7RS,9aRS)-2-furan-2-yl-5-[7-(isoquinolin-5-yloxymethyl)-octahydro-pyrido[1,2-a]pyrazin-2-yl]-[1,2,4]triazolo[1,5-a][1,3,5]triazin-7-ylamine;

(7RS,9aRS)-2-furan-2-yl-5-[7-(1H-pyrazolo[3,4-d]pyrimidin-4-yloxymethyl)-octahydro-pyrido[1,2-a]pyrazin-2-yl]-[1,2,4]triazolo[1,5-a][1,3,5]triazin-7-ylamine;

(7RS,9aRS)-2-furan-2-yl-5-(7-imidazol-1-ylmethyl-octahydro-pyrido[1,2-a]pyrazin-2-yl)-[1,2,4]triazolo[1,5-a][1,3,5]triazin-7-ylamine;

(7RS,9aRS)-2-furan-2-yl-5-(7-[1,2,4]triazol-1-ylmethyl-octahydro-pyrido[1,2-a]pyrazin-2-yl)]-[1,2,4]triazolo[1,5-a][1,3,5]triazin-7-ylamine;

(7RS,9aRS)-2-furan-2-yl-5-[7-(quinolin-2-yloxymethyl)-octahydro-pyrido[1,2-a]pyrazin-2-yl]-[1,2,4]triazolo[1,5-a][1,3,5]triazin-7-ylamine;

(6RS,9aRS)-2-furan-2-yl-5-(6-phenoxymethyl-octahydro-pyrido[1,2-a]pyrazin-2-yl)-[1,2,4]triazolo[1,5-a][1,3,5]triazin-7-ylamine;

(7RS,9aRS)-2-furan-2-yl-N-5-(2-pyrimidin-2-yl-octahydro-pyrido[1,2-a]pyrazin-7-ylmethyl)-[1,2,4]triazolo[1,5-a][1,3,5]triazine-5,7-diamine;

(7RS,9aRS)-5-(7-aminomethyl-octahydro-pyrido[1,2-a]pyrazin-2-yl)-2-furan-2-yl-[1,2,4]triazolo[1,5-a][1,3,5]triazin-7-ylamine;

(7RS,9aSR)-5-(7-aminomethyl-octahydro-pyrido[1,2-a]pyrazin-2-yl)-2-furan-2-yl-[1,2,4]triazolo[1,5-a][1,3,5]triazin-7-ylamine;

(7RS,9aRS)-5-{7-[(2,4-difluoro-benzylamino)-methyl]-octahydro-pyrido[1,2-a]pyrazin-2-yl}-2-furan-2-yl-[1,2,4]triazolo[1,5-a][1,3,5]triazin-7-ylamine;

(7RS,9aRS)-5-{7-[(bis-pyridin-4-ylmethyl-amino)-methyl]-octahydro-pyrido[1,2-a]pyrazin-2-yl}-2-furan-2-yl-[1,2,4]triazolo[1,5-a][1,3,5]triazin-7-ylamine;

(7RS,9aRS)-2-furan-2-yl-5-(7-{[(pyridin-4-ylmethyl)-amino]-methyl}-octahydro-pyrido[1,2-a]pyrazin-2-yl)-[1,2,4]triazolo[1,5-a][1,3,5]triazin-7-ylamine;

(7RS,9aRS)-5-{7-[(bis-pyridin-2-ylmethyl-amino)-methyl]-octahydro-pyrido[1,2-a]pyrazin-2-yl}-2-furan-2-yl-[1,2,4]triazolo[1,5-a][1,3,5]triazin-7-ylamine;

(7RS,9aRS)-5-{7-[(bis-pyridin-3-ylmethyl-amino)-methyl]-octahydro-pyrido[1,2-a]pyrazin-2-yl}-2-furan-2-yl-[1,2,4]triazolo[1,5-a][1,3,5]triazin-7-ylamine;

(7RS,9aRS)-2-furan-2-yl-5-[7-(pyrimidin-2-ylaminomethyl)-octahydro-pyrido[1,2-a]pyrazin-2-yl]-[1,2,4]triazolo[1,5-a][1,3,5]triazin-7-ylamine;

(7RS,9aRS)-5-(7-{[(5-chloro-1,3-dimethyl-1H-pyrazol-4-ylmethyl)-amino]-methyl}-octahydro-pyrido[1,2-a]pyrazin-2-yl)-2-furan-2-yl-[1,2,4]triazolo[1,5-a][1,3,5]triazin-7-ylamine;

(7RS,9aSR)-5-{7-[(bis-pyridin-3-ylmethyl-amino)-methyl]-octahydro-pyrido[1,2-a]pyrazin-2-yl}-2-furan-2-yl-[1,2,4]triazolo[1,5-a][1,3,5]triazin-7-ylamine;

(R)-2-furan-2-yl-5-(hexahydro-pyrrolo[1,2-a]pyrazin-2-yl)-[1,2,4]triazolo[1,5-a][1,3,5]triazin-7-ylamine; and (7RS, 9aRS)-2-furan-2-yl-5-[7-(quinolin-7-yloxymethyl)-octahydro-pyrido[1,2-a]pyrazin-2-yl]-[1,2,4]triazolo[1,5-a][1,3,5]triazin-7-ylamine.

24. The compound of claim 1, said compound being selected from the group consisting of:

(7RS,9aRS)-2-furan-2-yl-5-[7-(quinolin-6-yloxymethyl)-octahydro-pyrido[1,2-a]pyrazin-2-yl]-[1,2,4]triazolo[1,5-a][1,3,5]triazin-7-ylamine;

(7RS,9aRS)-5-[7-(3-fluoro-phenoxymethyl)-octahydro-pyrido[1,2-a]pyrazin-2-yl]-2-furan-2-yl-]-[1,2,4]triazolo[1,5-a][1,3,5]triazin-7-ylamine;

(7RS,9aRS)-2-furan-2-yl-N-5-(2-pyrimidin-2-yl-octahydro-pyrido[1,2-a]pyrazin-7-ylmethyl)-[1,2,4]triazolo[1,5-a][1,3,5]triazine-5,7-diamine;

(7RS,9aRS)-5-{7-[(bis-pyridin-3-ylmethyl-amino)-methyl]-octahydro-pyrido[1,2-a]pyrazin-2-yl}-2-furan-2-yl-[1,2,4]triazolo[1,5-a][1,3,5]triazin-7-ylamine; and (7RS, 9aRS)-2-furan-2-yl-5-[7-(quinolin-7-yloxymethyl)-octahydro-pyrido[1,2-a]pyrazin-2-yl]-[1,2,4]triazolo[1,5-a][1,3,5]triazin-7-ylamine.

25. A pharmaceutical composition comprising a compound of claim 1 and a pharmaceutically acceptable carrier.

26. A pharmaceutical composition comprising a compound of claim 22 and a pharmaceutically acceptable carrier.

27. A method of treating Parkinson's disease in a subject, the method comprising the step of administering to said subject an effective amount of a compound of claim 1.

* * * * *